United States Patent
Gerber et al.

(10) Patent No.: US 9,185,489 B2
(45) Date of Patent: Nov. 10, 2015

(54) AUTOMATIC VOIDING DIARY

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 2228 days.

(21) Appl. No.: 11/755,559

(22) Filed: May 30, 2007

(65) Prior Publication Data

US 2008/0300649 A1 Dec. 4, 2008

(51) Int. Cl.
*A61N 1/36* (2006.01)
*H04R 5/02* (2006.01)
*A61F 13/42* (2006.01)
*A61B 5/00* (2006.01)
*A61B 5/20* (2006.01)
*A61B 7/00* (2006.01)
(Continued)

(52) U.S. Cl.
CPC .............. *H04R 5/023* (2013.01); *A61B 5/0031* (2013.01); *A61B 5/202* (2013.01); *A61B 5/204* (2013.01); *A61B 5/205* (2013.01); *A61B 5/6846* (2013.01); *A61B 7/008* (2013.01); *A61F 13/42* (2013.01); *A61N 1/36007* (2013.01); *A61N 1/37211* (2013.01); *A61B 5/14507* (2013.01)

(58) Field of Classification Search
CPC ........... A61N 1/36007; A61N 1/37211; A61B 5/208; A61B 5/14507; A61B 5/202; A61B 5/0031; A61B 5/204; A61B 5/205; A61B 5/6846; A61B 2562/0204; A61B 7/008; A61F 13/42; H04R 5/023
USPC .......... 600/541, 30; 607/39, 41, 133, 138, 40; 128/898
See application file for complete search history.

(56) References Cited

U.S. PATENT DOCUMENTS

| | | |
|---|---|---|
| 3,363,619 A | 1/1968 | Keitzer |
| 4,813,422 A | 3/1989 | Fisher et al. |

(Continued)

FOREIGN PATENT DOCUMENTS

| | | |
|---|---|---|
| GB | 2424075 | 8/2006 |
| WO | WO 00/56242 | 9/2000 |

(Continued)

OTHER PUBLICATIONS

U.S. Appl. No. 11/414,504, entitled, "Voiding Detection With Learning Mode," filed Apr. 28, 2006.

(Continued)

*Primary Examiner* — Christopher D Koharski
*Assistant Examiner* — Pamela M Bays
(74) *Attorney, Agent, or Firm* — Shumaker & Sieffert, P.A.

(57) ABSTRACT

A device that may be used as an automatic voiding diary detects urinary and/or fecal voiding events and records voiding information indicative of the voiding events without the need for significant patient interaction. The device includes a microphone that captures internal and/or external sounds that are associated with voiding events and generates an electrical signal based the sounds. The device processes the electrical signal to determine whether the signal is indicative of the occurrence of a voiding event (i.e., the device detects voiding events) by, for example, comparing the electrical signal to a signal template or comparing an amplitude of the signal to a threshold. The device may be a device implanted within the patient or an external device that can be carried or attached to the body or clothing of the patient.

23 Claims, 19 Drawing Sheets

(51) Int. Cl.
 *A61N 1/372* (2006.01)
 *A61B 5/145* (2006.01)

(56) References Cited

U.S. PATENT DOCUMENTS

| | | | |
|---|---|---|---|
| 5,304,206 | A | 4/1994 | Baker, Jr. et al. |
| 5,959,535 | A | 9/1999 | Remsburg |
| 6,354,991 | B1 | 3/2002 | Gross et al. |
| 6,638,208 | B1 | 10/2003 | Natarajan et al. |
| 6,652,449 | B1 | 11/2003 | Gross et al. |
| 6,941,171 | B2 | 9/2005 | Mann et al. |
| 2002/0055779 | A1 | 5/2002 | Andrews |
| 2004/0093093 | A1 | 5/2004 | Andrews |
| 2004/0267086 | A1 | 12/2004 | Anstadt et al. |
| 2005/0038380 | A1 | 2/2005 | Nemir et al. |
| 2005/0143779 | A1 | 6/2005 | Libbus |
| 2005/0149136 | A1* | 7/2005 | Siejko et al. ............... 607/17 |
| 2005/0195085 | A1* | 9/2005 | Cretu-Petra ............ 340/573.5 |
| 2005/0209644 | A1 | 9/2005 | Heruth et al. |
| 2006/0020225 | A1* | 1/2006 | Gerber et al. ............ 600/561 |
| 2006/0064037 | A1 | 3/2006 | Shalon et al. |
| 2006/0074458 | A1 | 4/2006 | Imran |
| 2006/0190046 | A9* | 8/2006 | Gerber .................... 607/39 |
| 2006/0190050 | A1 | 8/2006 | Gerber et al. |
| 2006/0190051 | A1 | 8/2006 | Gerber et al. |
| 2007/0113649 | A1 | 5/2007 | Bharti et al. |
| 2007/0255176 | A1 | 11/2007 | Rondoni et al. |

FOREIGN PATENT DOCUMENTS

| | | |
|---|---|---|
| WO | WO 03/018106 | 3/2003 |
| WO | WO 03/066163 | 8/2003 |
| WO | WO2005/053793 A1 | 6/2005 |
| WO | WO 2006/041738 | 4/2006 |
| WO | WO 2007/137162 A2 | 11/2007 |

OTHER PUBLICATIONS

U.S. Appl. No. 11/117,058, entitled, "Implantable Medical Device Providing Adaptive Neurstimulation Therapy for Incontinence," filed Apr. 28, 2005.
U.S. Appl. No. 11/755,587, entitled, "Voiding Event Identification Based on Patient Input," filed May 30, 2007.
U.S. Appl. No. 11/755,578, entitled, "Implantable Medical Lead Including Voiding Event Sensor," filed May 30, 2007.
Notification of Transmittal of the International Search Report and the Written Opinion of the International Searching Authority, or the Declaration for corresponding patent application No. PCT/US2008/061500, mailed Aug. 6, 2008, 15 pages.
Communication pursuant to Article 94(3) EPC, dated Aug. 23, 2011, for counterpart European Patent Application No. 08 746 848.4, 5 pages.
Response to Examination Report dated Aug. 23, 2011, from counterpart European Patent Application No. 08746848.4, dated Feb. 29, 2012, 4 pages.
Prosecution History from U.S. Appl. No. 11/755,587, dated Apr. 9, 2010 through Jan. 20, 2012, 127 pages.
Prosecution History from U.S. Appl. No. 11/755,578. dated Aug. 20, 2010 through Sep. 27, 2012, 98 pages.

* cited by examiner

AUTOMATIC VOIDING DIARY

TECHNICAL FIELD

The invention relates to medical devices and, more particularly, devices for the treatment or diagnosis of urinary or fecal incontinence.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Monitoring urinary incontinence aids a clinician in diagnosing the precise condition of the patient. For example, a clinician may monitor parameters of voiding events, such as time of voiding events (voluntary and involuntary), volume of leaked fluid for an event, number of voiding events, and contents of urine, in order to diagnose the condition of the patient. Accordingly, monitoring may include collecting urine samples from the patient and/or maintaining a patient voiding diary in which the patient logs voluntary voiding events, involuntary voiding events, i.e., leakage, or other related problems. The patient may keep the voiding diary on paper or in an electronic device. The clinician may review the samples to determine the contents of the urine and may review the diary to view the frequency and number of voiding events experienced by the patient. In some cases, the clinician may tailor a therapy, such as electrical stimulation, according to the diary and the contents of the urine samples.

SUMMARY

This disclosure describes methods and systems for maintaining an automatic voiding diary. The device detects urinary or fecal voiding events by processing a signal generated by a sensor and records voiding information for the detected voiding events. The voiding information is wirelessly transmitted to an external device, such as a patient or clinician programmer, that presents the voiding information to an authorized user, such as a clinician. The voiding information obtained over a series of voiding events forms an automated voiding diary that is useful for diagnosing a condition of the patient and determining the efficacy of therapy delivered to treat urinary or fecal incontinence. A clinician may also manually adjust therapy parameters based on the voiding information. In some embodiments, the device may include therapy elements or communicate with a therapy delivery device to deliver therapy, e.g., electrical stimulation, drug therapy, or a combination of both, or automatically adjust therapy parameters based on the voiding information.

Maintaining an accurate voiding diary is often difficult for a patient. With some manually-maintained voiding diaries, the patient manually tracks voiding event, such as by manually writing down the date and time of the voiding event or providing an input via an electronic device. With manual voiding diaries, there may be a risk that the patient may neglect or forget to record all the necessary information. For example, a patient may neglect or forget to record the time at which the voiding event occurred or identify the voiding event as a voluntary or involuntary event. A manual diary can also be inaccurate because entries by the patient are subjective and may be influenced by embarrassment or other issues.

This disclosure describes various systems and methods that provide an automatic voiding diary that records a patient's voiding events without the need for significant patient interaction. In one embodiment, the automatic voiding diary detects voiding events based on an electrical signal generated by a microphone. The microphone may be a crystal microphone, condenser microphone, a ribbon microphone, or other type of microphone. The microphone translates sounds associated with voiding events into an electrical signal. The sounds may be internal sounds of the patient or external sounds. Internal sounds may be sounds generated by the bladder, urinary tract, rectum, intestines, or other organs and tissue that produce noise indicative of a urinary or fecal voiding event. External sounds may include sounds produced by the patient or environment during a voiding event, such as fluid being voided into a toilet, flushing of a toilet, fluid exiting an opening in the urethra of the patient, or other sound associated with voiding events.

Detecting voiding events based on the electrical signal generated by the microphone may involve processing the signal by, for example, comparing or correlating the electrical signal with a voiding signature stored in memory. The voiding signature includes a characteristic of an electrical signal that is generated during an actual voiding event for a patient. In one embodiment, the voiding signature used to detect voiding events is an example signal generated by the microphone during an actual voiding event. The voiding signature may be individualized to a particular patient or may be applicable to more than one patient. This example signal is referred to as a signal template. In this way, the automatic voiding diary may utilize an initial training or calibration mode to establish a voiding signature, i.e., capture a signal template, that can be used to detect a voiding signature in the signal generated by the microphone.

The automatic voiding diary may be configured as an implantable medical device (IMD) or an external device. When implemented as an IMD, the microphone may be located on or within a housing of the IMD or on a lead coupled to an IMD. In one example embodiment, the IMD may be configured as an independent diagnostic device that wirelessly communicates with an implantable therapy delivery device, such as an implantable neurostimulator (INS) or implantable drug pump, and external programmers for the implantable therapy delivery device. In another example embodiment, the automatic voiding diary may be configured as an IMD that operates as an automatic voiding diary and a therapy delivery device.

When implemented as an external device, the automatic voiding diary may be implemented as part of a personal digital assistant (PDA), cell phone, watch, programmer for an INS or other implantable therapy delivery device, or other personal electronic device. Alternatively, the automatic voiding diary may be implemented as a dedicated device that the patient may carry or attach to clothing. In any case, the automatic voiding diary may be configured to communicate with a implantable therapy delivery device and programmers for the implantable therapy delivery device.

In some embodiments, a device may include a feature for identifying detected voiding events as voluntary or involuntary events based on a patient defined action. The user friendly feature is useful for maintaining a substantially automatic voiding diary implanted in the patient to identify an automatically detected voiding event based on a patient defined action. For example, the patient defined action may include manually tapping the skin located proximate to the automatic voiding diary. In this example, the automatic voiding diary includes an accelerometer that generates an electrical signal based on one or more characteristics of the tapping, e.g., the number, frequency, and duration. The automatic voiding diary processes the accelerometer signal and records the appropriate identification information in memory.

In some embodiments, the lack of a patient defined action may be used to provide additional information. For example, an automatically detected voiding event may be identified as a false positive when a patient defined action is not received within a pre-determined period of time following the detection of the event. Identifying voiding events based on a patient defined action that is detected via an implanted medical device may eliminate the need for the patient to carry a separate external programmer to enter identification information for detected voiding events. The identification information in the voiding diary may be particularly useful to a clinician for determining the efficacy of therapy and manually adjusting therapy parameters. In one embodiment, a therapy delivery device automatically adjust therapy parameters or deliver therapy to prevent or reduce involuntary voiding events in the future in response to the automatic voiding diary receiving input, i.e., a patient defined action, that identifies a voiding event as an involuntary event.

In another example embodiment, an implantable medical lead that carries one or more sensors is coupled to the automatic voiding diary or, more specifically, a device that includes the automatic voiding diary. The elongated body of the medical lead extends between a proximal end coupled to the automatic voiding diary device and a distal end that carries the one or more sensors. The automatic voiding diary device processes the signals generated by the sensors to detect voiding events. The sensors may be one or more microphones, pressure sensors, flow sensors, strain gauges, sensing electrodes, temperature sensors, or any other type of sensor used for sensing a parameter associated with voiding events.

The lead may be particularly advantageous in embodiments that use the automatic voiding diary device in combination with a therapy delivery device. In such embodiments, the lead may be introduced to a target sensing site in the same way as a therapy lead is introduced to a target therapy site. In other words, although the target sensing and stimulation sites may be at different locations, the leads can be introduced through a single incision. For example, a target therapy site may be proximate to a sacral nerve, such as the S3 sacral nerve. Typically, a therapy lead, i.e., a lead carrying stimulation electrodes or a fluid delivery device that delivers one or more drugs, is introduced into the S3 sacral foramen to access the sacral nerve. Stimulation of the S3 sacral nerve may help treat urinary and fecal control disorders. In this case, the sensing lead described in this disclosure is introduced through the same or a different foramen and positioned or guided to the target sensing site. In this way, additional trauma to the patient attributable to the implantation of the sensing lead is avoided.

Further, some embodiments may utilize a combination lead. A combination lead carries sensors for detecting voiding events proximate to its distal end and delivers therapy for urinary or fecal incontinence. One example of a combination lead is a medical lead that includes one or more stimulation electrodes. The stimulation electrodes may be located adjacent to the sensors proximate to the distal end of the lead, interspersed with the sensors at the distal end, for example, in an alternating fashion, or otherwise positioned anywhere along the length of the lead. Another example of a combination lead in accordance with the present invention is a fluid delivery device for delivering one or more drugs that carries the sensors at the distal end.

A combination lead that may be particularly advantageous includes stimulation electrodes or openings for delivering drugs along a medially located portion of the lead. In this case, the lead can be positioned so that when it is fully inserted, the stimulation electrodes or openings for delivering drug therapy are positioned at the target stimulation site, such as proximate to the S3 sacral nerve, and the sensors are positioned at the target sensing site, such as proximate to a portion of the bladder, intestines, or rectum.

In one embodiment, the invention is directed towards a system comprising a microphone that generates an electrical signal based on a sound associated with a voiding event of a patient, and a processor that determines whether the voiding event occurred based on the electrical signal. The processor generates voiding information upon detecting an occurrence of the voiding event.

In another embodiment, the invention is directed towards a method of creating a voiding diary for a patient. The method comprises receiving an electrical signal from a microphone, where the microphone generates the electrical signal based on a sound associated with a voiding event, determining whether the voiding event occurred based on the electrical signal, and generating voiding information upon detecting the occurrence of the voiding event.

In another embodiment, the invention is directed towards a computer-readable medium comprising instructions that cause a processor to receive an electrical signal from a microphone, where the microphone generates the electrical signal based on a sound associated with a voiding event, determine whether the voiding event occurred based on the electrical signal, and generate voiding information upon detecting the occurrence of the voiding event.

In various embodiments, the invention may provide one or more advantages. For example, the automatic voiding diary records voiding events without the need for significant patient interaction and may be implanted within the patient, incorporated as part of a personal electronic device, or implemented as a wearable electronic device that automatically generates a voiding log. This may eliminate the need for a patient to keep a manual diary and, therefore, may provide a more objective and accurate log for review by a clinician and therapy based on the log.

In addition, information from the automatic voiding diary may be used in a closed loop system implemented by the automatic voiding diary or associated IMD to automatically adjust stimulation parameters based on the measured parameters, detected voiding events or an identification of voiding events as controlled or involuntary. In this manner, the automatic voiding diary may provide adjustment to the therapy in response to detecting an involuntary voiding event. Consequently, the automatic voiding diary may, for example, control a stimulator that stimulates a nerve or muscle of the patient to prevent the patient from unintentionally voiding his or her bladder in response to detecting voiding events.

In embodiments in which the automatic voiding diary records identification data for voiding events based on a patient defined action, the additional input may be useful for diagnosis of the patient and selection of a therapy for the patient.

The details of one or more embodiments of the invention are set forth in the accompanying drawings and the description below. Other features, objects, and advantages of the invention will be apparent from the description and drawings, and from the claims.

DETAILED DESCRIPTION

Urinary and fecal incontinence are conditions that affect the quality of life and health of many people. Urinary incontinence is an inability to control urinary function and is a common problem afflicting people of all ages, genders, and races. Likewise, fecal incontinence is an inability to control bowel movements. A variety of disorders may compromise performance of the urinary tract and anal sphincter and, thus, contribute to incontinence. Many of the disorders may be associated with aging, injury, or illness.

Tracking voiding events may be important for diagnosing a patient's condition, such as by determining the number of voluntary or involuntary events a patient has within a certain time range (e.g., a day or a week), or for selecting an appropriate course of treatment, which may or may not include stimulation therapy, for the patient to treat the incontinence. However, manually tracking voiding events, e.g., keeping a written or electronic voiding diary, is often undesirable or inconvenient for the patient. Keeping the voiding diary takes time out of the patient's day and may be noticed by other people, causing embarrassment to the patient. In addition, manually tracking voiding events may result in voiding information errors. For example, the patient may inadvertently forget to record an event, fail to objectively describe the event, or even purposefully keep false voiding information in the diary. These problems with a voiding diary may undermine the ability of the clinician to properly assess patient condition and prescribe an effective therapy.

Systems described herein include a device that is configured to operate as an automatic voiding diary for recording voiding events without the need for significant patient interaction. The device is referred throughout this disclosure as an automatic voiding diary and generally described for recording urinary voiding events. However, it should be understood that the automatic voiding diary may also be configured to record fecal voiding events.

Figure 1:
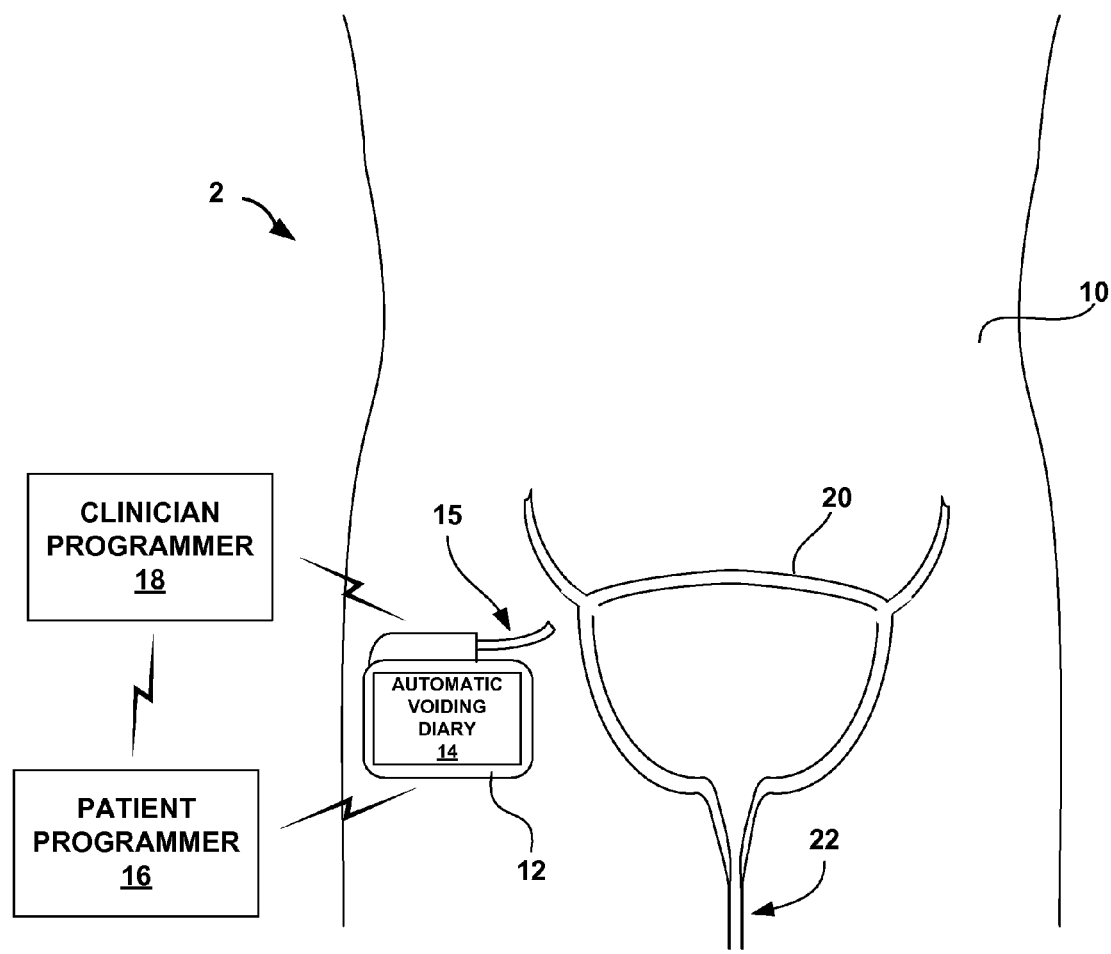
FIG. 1 is a schematic diagram illustrating an embodiment of a system including an implantable medical device (IMD) configured to operate as an automatic voiding diary and deliver therapy for treating urinary incontinence.

FIG. 1 is a schematic diagram illustrating a system 2 that includes an implantable medical device (IMD) 12 configured to automatically record urinary voiding events and deliver therapy to patient 10 for urinary incontinence. IMD 12 may also be configured to provide an alert for patient 10 to seek medical follow-up in response to, for example, detecting that the therapy delivered is inadequate or the efficacy of therapy is degrading. The alert may be provided via patient programmer 16 or other patient monitoring system (not shown). As shown in FIG. 1, system 2 includes IMD 12 and patient and clinician programmers 16 and 18, respectively, in wireless communication with IMD 12. IMD 12 delivers therapy to patient 10 for urinary incontinence via therapy element 15 and includes automatic voiding diary 14. In particular, automatic voiding diary 14 automatically records voiding events without the need for significant patient interaction. The voiding diary may be used to determine the efficacy of the therapy, e.g., by determining the number of controlled voiding events and involuntary voiding events during therapy delivery or by determining the therapy program being implemented by IMD 12 at the time the involuntary voiding events occurred. In addition, the voiding diary 14 may be used to manually or automatically adjust therapy parameters with which IMD 12 delivers therapy to patient 10 or trigger therapy delivery in response to detecting a voiding event.

In general, automatic voiding diary 14 detects urinary voiding events by receiving one or more electrical signals from a sensor that vary as a function of a parameter associated with a voiding event and processes the electrical signals generated by the one or more sensors to generate voiding information. The voiding information may be recorded for the detected urinary voiding events. The parameter associated with a voiding event (i.e., a voiding parameter) may include, for example, pelvic nerve activity, the content of leaked fluid, amount of leaked fluid, temperature of leaked fluid, pH of the leaked fluid, bladder volume, bladder pressure, sphincter pressure, bladder impedance, volume of voided fluid, or a sound associated with the voiding event. The one or more sensors may generate the signal may include, for example, one or more microphones, pressure sensors, flow sensors, strain gauges, sensing electrodes, temperature sensors, any other type of sensor used for generating a signal indicative of a parameter associated with voiding events, or any combination thereof. In the case of measuring bladder impedance, the impedance may be measured between at least two electrodes positioned at different locations on the bladder.

The voiding information may be wirelessly transmitted to one or both of patient and clinician programmers 16 and 18 or another computing device. Patient and clinician programmers 16 and 18 may present the voiding information to an authorized user, e.g., a patient and clinician, respectively, as a voiding diary or log. As described in further detail in this disclosure, a patient may review the voiding diary to manually adjust therapy parameters within pre-determined settings and/or confirm the voiding information. A clinician may review the voiding information for diagnostic purposes, i.e., monitor the condition of the patient, to evaluate the efficacy of IMD 12 or of particular therapy programs including one or more therapy parameters implemented by IMD, or to manually adjust therapy parameters. Patient and clinician programmers 16 and 18 may also, in response to receiving the voiding information, automatically adjust one or more therapy parameters based on the received voiding information.

In FIG. 1, automatic voiding diary 14 includes a microphone (not shown) that translates sounds associated with a urinary voiding event into an electrical signal. The microphone may be a crystal microphone, condenser microphone, a ribbon microphone, or other type of microphone suitable for implantation within patient 10. The microphone may be positioned on or within the housing of IMD 12 or carried on therapy element 15, which may be, e.g., a medical lead or a fluid delivery catheter. In particular, the microphone in automatic voiding diary 14 may translate internal or external sounds into an electrical signal. Internal sounds may be sounds internal to patient 10, such as sounds produced by bladder 20, urinary tract 22, or other organs and tissue (not shown) that produce a sound associated with a urinary voiding event. External sounds may be sounds produced by patient 10 or the environment during a voiding event. An external sound, for example, may be a sound produced by urine being voided into a toilet, a toilet flushing, urine exiting urinary tract 22, urine being voided into an undergarment, or other sounds associated with a urinary voiding event.

In embodiments in which automatic voiding diary 14 is used for recording fecal voiding events, internal sounds may include sounds produced by the rectum (not shown), intestines (not shown), such as sounds produced by fecal matter moving through the bowel during a voiding event, or other organs and tissue (not shown) that produce sounds associated with a fecal voiding event. External sounds include sounds produced by patient 10 or the environment during a fecal voiding event, such as feces being voided into a toilet, a toilet flushing, feces exiting the rectum, feces being voided into an undergarment, or other sounds associated with a fecal voiding event.

IMD 12 may typically be subcutaneously implanted the body of patient 10, e.g., in the lower back, lower abdomen, or buttocks of patient 10. When implanted at one of these locations, a microphone positioned on or within the housing of IMD 12 may be capable of reliably picking up internal and/or external sounds associated with voiding events. Alternatively, the microphone may be carried on therapy element 15 coupled to IMD 12. In this case, therapy element 15 and, more particularly, the microphone carried by therapy element 15 is positioned at a target sensing site that may enable the microphone to pick up internal or external sounds associated with voiding events. However, in some embodiments, IMD 12 may be implanted at the target sensing site, which may be proximate to a portion of bladder 20, urinary tract 22, or other organs or tissue that produce sounds associated with voiding events. In those embodiments, a microphone carried on or within the housing of IMD 12 may be placed at the target sensing site without the need for therapy element 15 or another member coupling the microphone to IMD 12. In another example embodiment, the microphone may be a wireless microphone configured to be implanted within patient 10 and communicate with IMD 12 or an external device, such as patient and clinician programmers 16 and 18.

In any case, the location at which the microphone is positioned may affect the quality of the signal produced by the microphone. For this reason, it may be desirable to position IMD 12, and in the case of an implanted microphone carried on therapy element 15 coupled to IMD 12, implant the therapy element 15 such that the microphone is proximate to the source of the sound that is to be detected in order to strengthen the signal produced by the microphone. In addition, the position of the microphone relative to the source of the sound (or near the source of multiple sounds) may allow the microphone to pick-up sounds associated with a voiding event without being significantly affected by unwanted noises. Unwanted noises are generally sounds that are not associated with a voiding event, such as noises produced by the digestive system of patient 10 or the environment surrounding patient 10.

The electrical signal generated by the microphone, also referred to as the sensor signal, is processed to detect voiding events. Processing the sensor signal may, for example, involve processing the signal to remove noise, i.e., unwanted signal components, and processing the signal to identify a voiding signature. In some embodiments, the voiding signature includes a characteristic of an electrical signal that is generated prior to or during an actual voiding event for a patient or for multiple patients. The voiding signature may be individualized to a particular patient or may be applicable to more than one patient. In one embodiment, the voiding signature used to detecting voiding events is an example signal generated by the microphone during an actual voiding event. This example signal is referred to as a signal template and may be obtained during an initial training or calibration session for voiding diary 14. The training session may take place in a clinical environment with controlled conditions. For example, the bladder of patient 10 may be manually filled and the corresponding voiding event may be recorded using automatic voiding diary 14. The signal may be examined and, if determined to be satisfactory, may be stored and used as a signal template for detecting voiding events. Multiple signals may also be generated during the voiding diary 14 training session and averaged or otherwise analyzed to generate a signal template that is representative of a voiding event for the patient.

In general, voiding diary 14 may include a processor that amplifies, samples, filters, or otherwise processes the sensor signal to remove noise and identify a voiding signature in the sensor signal. Processing the sensor signal to remove noise from the signal may enable voiding diary to detect voiding events more reliably. Noise may be introduced into the sensor signal by other sounds that are detected by the microphone or introduced into the sensor signal by the microphone itself.

Thus, voiding diary may include a processor that filters the sensor signal before processing the signal to identify a voiding signature. The sensor signal may be filtered using various signal processing techniques that may be applied to suppress signal components at one or more frequencies or range of frequencies.

In one example embodiment, processing the sensor signal to identify a voiding signature in the sensor signal involves temporally correlating the sensor signal with a signal template. This may be achieved by sampling the signal with a sliding "window" that defines a time range, and comparing the sample of the signal to a signal template to identify a signal that correlates well with the template. For example, a processor of IMD 12 or an external device may perform a correlation analysis by moving a window along a digitized plot of the amplitude of the signal generated by the microphone at regular intervals to define a sample of the signal from the microphone. The sample window is slid along the plot until a correlation is detected between the waveform of the signal template and the waveform of the sample of the microphone signal defined by the window. By moving the window at regular time intervals, multiple sample periods are defined. The correlation may be detected by, for example, matching multiple points between the template waveform and the waveform of the plot of the signal from the microphone over time, or by applying any suitable mathematical correlation algorithm between the sample in the sampling window and a corresponding set of samples stored in the signal template.

In some embodiments, processing the sensor signal to detect voiding events may be more complex than correlating the sensor signal with a signal template. That is, rather than comparing the entire sensor signal waveform to the signal template, preliminary signal processing may be applied to locate portion of the sensor signal that exhibits an increased likelihood of containing a voiding signature. In fact, the sensor signal may be substantially continuous and generated over large periods of time (e.g., over days, weeks or more) and, therefore, include large portions that do not correspond to voiding events. As a result, a less complex processing technique may be used to first determine the likelihood that a portion of the sensor signal contains a voiding signature. Example processing techniques that may be used during a preliminary analysis of the sensor signal include comparing an amplitude of the sensor signal to a threshold value. The amplitude may be an amplitude of a particular frequency component. Based on the comparison to the threshold value, the sensor signal may then be correlated with the signal template. Using a combination of processing techniques in this way may conserve battery power, which may be important to the life of IMD 12 because it may be expected to operate for weeks, months, or years on a single power source.

The processing techniques described in this disclosure should not be considered limiting of the invention as broadly in this disclosure in any way. Rather, the described processing techniques are merely exemplary and are intended to provide descriptive examples without taking focus away from the primary features of the invention.

When a voiding event is detected, automatic voiding diary 14 stores voiding information associated with the detected voiding event in local memory within voiding diary 14 (or IMD 12 in embodiments in which IMD 12 includes voiding diary 14). The voiding information may include, for example, the corresponding portion of the sensor signal that includes the voiding signature or data that indicates the occurrence of the detected voiding event. The voiding information may also include a timestamp that corresponds to the time at which the voiding event was detected.

Furthermore, in some embodiments, system 2 or, more particularly, IMD 12, may include additional sensors (not shown) that monitor other voiding parameters. Examples of other voiding parameters include the content of voided fluid, amount of voided fluid, temperature of voided fluid, pH of voided fluid, and the like. Accordingly, the additional sensors may include one or more of impedance sensors, strain gauges, temperature sensors, accelerometers, pH sensors, chemical sensors, and the like. In such embodiments, automatic voiding diary 14 stores voiding information that corresponds to these voiding parameters.

In operation, automatic voiding diary 14 detects voluntary or controlled events and involuntary or incontinence events. It is typically important to distinguish between voluntary and involuntary voiding events for diagnostic purposes. For this reason, the voiding information recorded by automatic voiding diary 14 may include information that identifies a detected event as a voluntary or involuntary event.

In one example embodiment, patient 10 may enter input into patient programmer 16 to identify a voiding event as a controlled (i.e., voluntary) or involuntary event. Patient 10 may, for example, activate one or more buttons, use a stylus, mouse, or other peripheral device to enter input on a graphical user interface. Patient programmer 16 may then, in response to receiving the input, wirelessly transmit corresponding identification information (e.g., an indication of whether the voiding event was voluntary or involuntary) to automatic voiding diary 14, which may associate the received identification information with the corresponding voiding information. In embodiments in which automatic voiding diary 14 transmits the voiding information to patient programmer 16 for storage, patient programmer 16 may store the identification information with or without transmitting the information to automatic voiding diary 14 and may associate the voiding information with the voiding event identification information.

Other techniques for generating identification information for voiding events may be employed in other embodiments. For example, in one embodiment, an involuntary voiding event may be detected via one or more sensors incorporated into an undergarment, as described in commonly-assigned U.S. patent application Ser. No. 11/414,504 to John C. Rondoni et al., entitled, "VOIDING DETECTION WITH LEARNING MODE" and filed on Apr. 28, 2006, the entire content of which is incorporated herein by reference. The one or more sensors detect the presence of fluid which indicates that wetting, and most likely, an involuntary voiding event has occurred. In some cases, the sensor may be also capable of also detecting fluid pH or other characteristic of the fluid to identify that the fluid is urine. In some embodiments, a pocket that holds a sensor may also include absorption material that absorbs voided urine, such that the undergarment is similar to a diaper or protective garment.

In some embodiments, automatic voiding diary 14 includes features for storing voiding information, such as information that identifies a detected voiding event as a voluntary or involuntary event, based on a patient defined action, such as patient 10 tapping on the skin located above IMD 12. Such an example embodiment is illustrated and described in detail in FIGS. 12 and 13.

Various embodiments of automatic voiding diary 14 may be used for storing and retrieving the voiding information. In one example embodiment, automatic voiding diary 14 automatically records voiding information in local memory and wirelessly transmits the voiding information to patient programmer 16, clinician programmer 18, or both. Automatic voiding diary 14 may transmit the voiding information on request, periodically, or when local memory is full. Alternatively, automatic voiding diary 14 may transmit the voiding information substantially continuously.

In some embodiments, patient programmer 16 and clinician programmer 18 may retrieve information stored within automatic voiding diary 14 at any time, for example, by transmitting a wireless request signal to automatic voiding diary 14. In response to the request, automatic voiding diary 14 wireless transmits the voiding diary to the appropriate programmer which displays the voiding information as a diary or log to the user.

In other embodiments, automatic voiding diary 14 may transmit the stored voiding information to programmers 16 and 18 periodically. For example, automatic voiding diary 14 may store voiding information for a pre-determined period of time, such as approximately one day, and transmit the voiding information at the end of the time period. In this case, automatic voiding diary 14 may erase or record over the transmitted voiding information.

In another example, automatic voiding diary 14 may transmit the voiding information to one or both of programmer 16 and 18 when local memory is full or near full capacity. In this case, automatic voiding diary 14 may erase or record over the stored data when the voiding information has been successfully transmitted. In this way, automatic voiding diary 14 may efficiently store voiding information and then "dump" the stored information to patient programmer 16 for long term storage. Alternatively, automatic voiding diary 14 may store voiding information until local memory is full or near capacity and transmit all subsequent voiding information to patient programmer 16.

In an additional example, automatic voiding diary 14 may store little or no voiding information. In this case, diary 14 processes the sensor signal to detect a voiding event, generate the voiding information, and immediately transmits the voiding information to patient programmer 16 for long term storage. The voiding information may be stored in memory of diary 14 for a short period of time or may be transmitted substantially directly to patient programmer 16. As a result, diary 14, in this case, may require a relatively small amount of memory.

The amount of voiding information stored in automatic voiding diary 14 is related to the size of local memory of automatic voiding diary 14. Storing a smaller amount of voiding information in local memory of automatic voiding diary 14 allows the size of diary 14 and, thus, the size of IMD 12 to be reduced. The tradeoff between size and the memory capacity of automatic voiding diary 14 is a design choice that may be affected by various other aspects of system 2.

In general, programmers 16 and 18 provide an easy to user interface for viewing the voiding diary and adjusting and/or programming therapy. The interface may include tools for navigating and customizing the display. For example, programmers 16 and 18 may provide a scroll bar or other mechanism for navigating the voiding diary and a menu or selection mechanism for specifying the information that is to be displayed in the voiding diary. Programmers 16 and 18 communicate with IMD 12 via a wireless interface. Example wireless interfaces include wireless telemetry, Bluetooth, IEEE 802.11 (a), (b), (g), Medical Implant Communication Services (MICS), and other standard proprietary wireless interfaces.

Patient 10 may use patient programmer 16 to review voiding information and, in some embodiments, enter input to verify that the information is correct. Patient 10 may also user programmer 16 to identify an abnormal intake of fluid, such as a drinking binge, or other event that may affect a normal voiding pattern. In this way, patient 10 can use patient programmer 16 to ensure that the data stored in voiding diary 14 is accurate.

For example, after patient 10 voids bladder 22 voluntarily or involuntarily, patient 10 may use programmer 16 to verify that automatic voiding diary 14 detected the event and identify or categorize the event as a controlled or involuntary event. Verifying the information may involve entering input into programmer 16. For example, patient programmer 16 may prompt patient 10 via one or more questions, to which patient 10 may enter responses via a user interface of patient programmer 16. In the event that patient 10 indicates that the voiding information generated by automatic voiding diary 14 is incorrect, automatic voiding diary 14 may discard the incorrect information or, alternatively, store additional data that indicates that patient 10 identified the information as being incorrect. Storing this data may prevent or deter patient 10 from falsely modifying information because of embarrassment or other reasons since the clinician will be able to determine if the information has been modified.

A clinician or other authorized user may use clinician programmer 18 to view the voiding diary and use the voiding diary to identify a condition afflicting patient 10 or monitor a condition of patient 10. In this way, a clinician can use programmer 18 as a diagnostic tool to determine the appropriate course of treatment, which may or may not include therapy, or determine the efficacy of treatment. As an example, a clinician may diagnose that patient 10 suffers from nocturnal enuresis by examining the time and nature of voiding events over a period of time within the voiding diary. Based on the diagnosis, the clinician may prescribe therapy in the form of stimulation therapy, drug therapy, or a combination of both. The clinician may then use programmer 18 at a later date to view the voiding diary to evaluate the efficacy of the treatment.

Additionally, a clinician or other authorized user may use clinician programmer 18 to program therapy for patient 10, such as therapy for urinary incontinence. Programmer 18 may transmit one or more programming instructions to IMD 12 via wireless communication signals. The programming instructions may specify one or more therapy programs that IMD 12 may deliver therapy in accordance with, where each therapy program defines one or more therapy parameters. Examples of therapy parameters include voltage or current amplitude, pulse width or pulse frequency of electrical stimulation, or drug bolus size, drug concentration or frequency of drug delivery. The type of therapy parameters depends on the type of therapy delivered by IMD 12.

In the example illustrated in FIG. 1, programmer 18 may be configured to program IMD 12 to deliver stimulation therapy, drug therapy, or a combination of both according to one or more therapy programs. Accordingly, in some embodiments, IMD 12 may operate as an implantable neurostimulator (INS) that delivers electrical stimulation therapy for incontinence, while in other embodiments, IMD 12 may be a drug delivery device that delivers one or more drugs. In another embodiment, IMD 12 may be configured to operate as an INS and a drug delivery device.

Accordingly, therapy element 15 in FIG. 1 may represent a lead carrying one or more electrodes that delivery stimulation in the form of electrical pulses or a fluid delivery device, such as a catheter, that delivers one or more drugs. In some embodiments, therapy element 15 may carry electrodes and deliver drugs. Therefore, therapy element 15 should not be considered limiting of the invention as broadly described in this disclosure. Instead it is the purpose of therapy element 15 to represent one or many therapy elements that deliver therapy from IMD 12 to a target tissue site within patient 10 in the form of electrical stimulation, drugs, or a combination of both. Therefore, it should be understood that FIG. 1 illustrates one of the many example embodiments that fall within the scope of the invention as broadly described in this disclosure.

Programming therapy may involve selecting or adjusting stimulation parameters or drug delivery parameters. As previously described, example stimulation parameters include an electrode configuration, a pulse rate, a pulse width, and voltage amplitude or current amplitude. Electrode configuration may refer to both a combination of selected electrodes and polarities of the electrodes, i.e., as a cathode or anode. Electrical stimulation may be delivered in accordance with one or more programs. Programs may deliver electrical stimulation in a variety of different modes, such as a continuous mode, in a series of bursts, or a combination of both. In a similar manner, a clinician may specify a set of parameters for drug delivery that includes selecting which drug or mixture of drugs to deliver, as well as the dosage and rate at which to deliver the selected drug or drugs.

In practice, a clinician may use clinician programmer 18 to select a set of initial therapy parameters and view the voiding diary after patient 10 has been subjected to therapy for a period of time. By comparing the voiding information before and after therapy, the clinician can determine the efficacy of the treatment and may manually adjust stimulation parameters in an attempt to improve the efficacy of the treatment. Patient programmer 16 may also provide certain limited capabilities to patient 10. For example, patient 10 may use programmer 16 to select particular programs or vary the intensity of therapy within a pre-determined range. Further, patient programmer 16 or IMD 12 itself may automatically adjust parameters according to the detected voiding information. For example, in response to detecting a voiding event and associating the voiding event with identification information that indicates the voiding event was involuntary, IMD 12 may automatically increase the intensity of therapy or otherwise adjust the therapy parameters to prevent or reduce involuntary voiding from occurring in the future.

Stimulation parameter adaptation logic that may be implemented by IMD 12, clinician programmer 18 or patient programmer 16 is discussed in commonly-assigned U.S. patent application Ser. No. 11/117,058, entitled, "IMPLANTABLE MEDICAL DEVICE PROVIDING ADAPTIVE NEUROSTIMULATION THERAPY FOR INCONTINENCE," and filed on Apr. 28, 2005, which is incorporated herein by reference in its entirety.

It should be understood that system 2 as illustrated in FIG. 1 depicts one of many example systems. That is, system 2, as depicted in FIG. 1, should not be considered limiting of the invention as broadly described in this disclosure in any way. Instead, the purpose of system 2 is to provide one example embodiment suitable for broadly describing features of the invention.

For example, although FIG. 1 illustrates a single device, i.e., IMD 12, which operates as a therapy delivery device and an automatic voiding diary, other example systems may include a therapy delivery device and a separate IMD configured to operate as an automatic voiding diary. In other words, the therapy delivery device and the automatic voiding diary device may be separate devices implanted within the patient, and in some embodiments, the therapy delivery device and automatic voiding diary may communicate via wired or wireless communication techniques. The devices may be implanted proximate to one another or at different locations within the patient. A system that includes a therapy delivery device and a separate automatic voiding diary device may be advantageous when the implant site for delivering therapy is different than the implant site for sensing sounds associated with a voiding event.

In other example embodiments, the automatic voiding diary device may be an external device. In such embodiments, the automatic voiding diary device may be incorporated with patient programmer 16 or implemented as a dedicated external device. In either case, it may be desirable for patient 10 to carry the external device substantially continuously during a voiding event information gathering period in order to obtain accurate voiding information. Additionally, it may be desirable for patient 10 to carry the external device may be required to be close to the body for the microphone to generate a signal based on an internal or external sound associated with a voiding event. The external device may be implemented in various ways. For example, the external device may be taped to the skin of patient 10 or an undergarment worn by patient 10, trapped between clothing and the skin of patient 10, attached to the inside of clothing worn by patient 10, sutured to the skin of patient 10, held to the skin of patient 10 via a strap, or may otherwise be wearable by patient 10.

In further example embodiments, the automatic voiding diary is not necessarily used in combination with a therapy delivery device. A system that does not include a therapy delivery device may be used as a diagnostic tool to identify and/or monitor the condition of the patient and also to determine if therapy would benefit the patient and which therapy would be most beneficial.

It is also contemplated that system 2 or other embodiments of the invention may be used in combination with one or more additional sensors that measure other voiding parameters (i.e., parameters associated with voiding). The monitoring of electrical signals indicative of voiding parameters may be useful for analyzing a patient's condition or therapy program. The additional sensors may include one or more of pressure sensors, impedance sensors, strain gauges, temperature sensors, accelerometers, pH sensors, chemical sensors, and the like. Accordingly, other voiding parameters of interest may include the content of leaked fluid, amount of leaked fluid, temperature of leaked fluid, pH of the leaked fluid, bladder pressure, and so forth. In addition, other parameters associated with a voiding event may also be monitored and stored in the voiding diary. For example, the activity and posture of patient 10 may also be stored in the voiding diary.

Automatic voiding diary 14 may store the output of the additional sensors in the voiding diary. Accordingly, a clinician may use clinician programmer 18 to view the voiding diary and adjust therapy parameters based on information relating to one or more voiding parameters stored within the voiding diary. Additionally, patient programmer 16, clinician programmer 18, or both may automatically adjust therapy parameters based on the information in the voiding diary. For example, the clinician or programmer 16 and 18 may increase the intensity of stimulation based one or more voiding parameters, such as the amount of fluid leaked, to prevent or reduce involuntary voiding.

Figure 2:
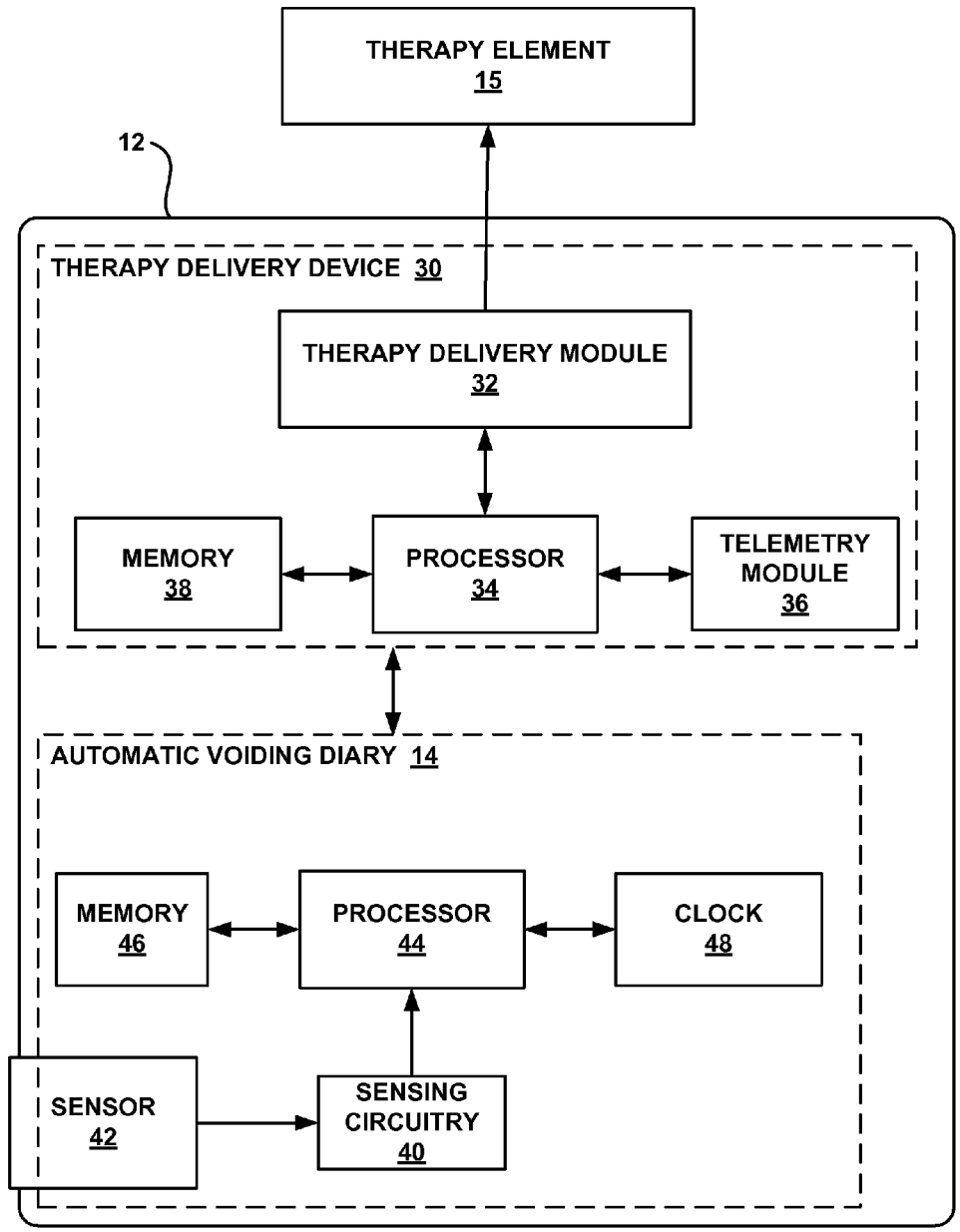
FIG. 2 is a block diagram illustrating components of the IMD of FIG. 1.

FIG. 2 is a block diagram illustrating various components of IMD 12. As shown in FIG. 2, IMD 12 includes components for automatic voiding diary 14 and components for therapy delivery device 30. In other embodiments, however, the components for automatic voiding diary 14 and therapy delivery device 30 may be enclosed in separate housings. The components of automatic voiding diary 14 record information associated with a voiding event without the need for significant interaction from patient 10. The components of therapy delivery device 30 deliver therapy to patient 10 to control urinary or fecal incontinence.

Automatic voiding diary 14 includes a sensing circuitry 40, sensor 42, processor 44, memory 46, and clock 48. In general, sensing circuitry 40 detects a voiding event based on the output of sensor 42, i.e., the electrical signal generated by sensor 42. Memory 46 stores voiding information under the control of processor 44. Processor 44 may obtain a clock signal from clock 48 to associate a timestamp with the voiding information for a detected voiding event stored in memory 46. Memory 46 may include any combination of volatile, non-volatile, removable, magnetic, optical, or solid state media, such as read-only memory (ROM), random access memory (RAM), electronically-erasable programmable ROM (EEPROM), flash memory, or the like. Processor 44 may include a microprocessor, microcontroller, digital signal processor (DSP), application specific integrated circuit (ASIC), field programmable gate array (FPGA), discrete logic circuitry, or a combination of such components.

In one embodiment, sensor 42 is a microphone that generates an electrical signal in accords with internal or external sounds associated with voiding events and may be positioned within or on the housing of IMD 12. Alternatively, sensor 42 may be carried within or on a lead that extends from IMD 12 or wirelessly coupled to IMD 12. In another embodiment, sensor 42 may be a wireless microphone implanted within patient 10 and configured to wirelessly communicate with IMD 12. As previously described, sensor 42 may be a crystal microphone, condenser microphone, a ribbon microphone, or other type of microphone suitable for implantation within patient 10.

In embodiments in which sensor 42 is a microphone, sensor 42 may generate a signal that varies as a function of internal sounds, such as sounds produced by bladder 20 (FIG. 1), urinary tract 22 (FIG. 1), rectum (not shown), intestines (not shown), such as sounds produced by fecal matter moving through the bowel during a voiding event, or other organs and tissue (not shown) of patient 10 that produce sounds associated with a urinary or fecal voiding event. In addition to or instead of generating the signals that vary as a function of internal sounds, sensor 42 may generate a signal that varies as a function of sounds external to patient 10, such as sounds produced by urine or feces being voided into a toilet, a toilet flushing, fluid exiting the opening of the urethra (FIG. 1), urine or feces being voided into an undergarment, a voice command, or other sound associated with a urinary or fecal voiding event.

The electrical signal output by sensor 42 may be amplified, filtered, and otherwise processed by sensing circuitry 40. As described above, sensing circuitry 40 may process the signal to remove unwanted signal components to more reliably detect a voiding event. Removing unwanted signal components, e.g., by filtering the output of sensor 42, may increase the likelihood of accurately and reliably detecting a voiding event. Unwanted signal components may include noise introduced by the signal path and signal components that result from sounds that are not associated with a voiding event but are picked up by sensor 42. These sounds may include other sounds internal to patient 10, such as digestive sounds, heart sounds, breathing sounds, and the like as well as sounds external to patient 10, i.e., sounds produced by the environment surrounding patient 10.

To detect a voiding event, sensing circuitry 40 may, for example, utilize a correlation or comparison technique, such as the temporal correlation technique described above. In particular, sensing circuitry 40 may apply the detection technique to the processed signal in which the unwanted signal components have been removed, i.e., the "clean" sensor signal. A correlation technique may involve correlating a sample of the signal generated by sensor 42 to a signal template stored in memory 46 in order to detect the presence of a voiding signature in the signal generated by sensor 42. The signal template may be generated based on one or more example signals that are produced by sensor 42 during a trial or test period. During the trial or test period, patient 10 may be instructed to void under controlled conditions. That is, patient 10 may void at a known time so the signal can be analyzed.

The voiding signature may be characterized by one or more signal characteristics, e.g., a particular frequency, amplitude, pattern, trend, or waveform shape, duration, or other signal characteristic. As an example, a sound associated with a voiding event, such as urine or feces being voiding into a toilet, may exhibit a particular frequency that lasts for several seconds or more. As another example, a sound produced by a muscle that contracts and relaxes to control voiding may be characterized by one or more pulses of sound at a particular frequency. In this case, the period of time between pulses may also be characteristic of the voiding signature.

Sensing circuitry 40 may employ various signal processing techniques to detect a voiding signature in the output of sensor 42. Example, correlation techniques may be performed in a time or frequency domain. In some cases, the frequency domain may be more revealing of signal characteristics than the time domain. Frequency analysis techniques involve converting the time domain signal produced by sensor 42 into a frequency signal. This can be achieved by applying a Fast Fourier Transform to the output of sensor 42, which is a time domain signal. Frequency analysis techniques may then be used to detect a voiding event in the frequency signal. Example frequency analysis techniques involve determining the power of the signal for particular frequency components.

Additional signal processing techniques may be used to conserve power. That is, because the detection processing techniques may be complex and consume significant power, sensing circuitry may also employ low power signal detection techniques. As an example, sensing circuitry 40 may compare the output of sensor 42 to a threshold value. The threshold value may be the total power of the sensor signal or power of a particular frequency. This comparison determines the likelihood that a particular portion of the sensor signal contains a voiding signature. In other words, when the amplitude of the output of sensor 42 exceeds the threshold, that portion of the signal has an increased likelihood of including a voiding signature. This may require little processing power as the technique involves a simple comparison between two values. However, when the signal exceeds the threshold, sensing circuit 40 may apply more complex and, therefore, power consuming detection techniques. In this way, IMD 12 may operate for several months or years relying on power from a finite power source (not shown), such as a rechargeable or nonrechargeable battery. In either case, power conservation is desirable.

In addition to storing a signal template or other voiding signatures, memory 46 of automatic voiding diary 14 may store voiding information associated with detected voiding events. In particular, processor 44 may generate voiding information based on the output of sensing circuitry 40 and store the information in memory 46. In one example, memory 46 stores data that indicates the occurrence of the detected event. Alternatively, memory 46 may store the actual signal generated by sensing circuitry 40 that contains the voiding signature. A clinician may retrieve the stored signals from memory 46 to analyze the signals. As previously described, memory 46 may also store other voiding information associated with a detected voiding event, such as a time stamp and data that identifies a detected event as a voluntary or involuntary event. In embodiments in which IMD 12 includes sensors for recording other voiding information, such as information associated with the contents of voided urine, this information is also stored in memory 46.

Processor 44 may associate a timestamp with a detected voiding event by sending a request signal to clock 48. In response to receiving the control signal, clock 48 generates a signal that represents the time. Alternatively, clock 48 may output the signal to processor 44 substantially continuously and processor 44 can examine the signal in response to detecting a voiding event. In any case, processor 44 may use the output of clock 48 to associate a timestamp with voiding information that is stored in memory 46.

In addition to voiding information, memory 46 may also store instructions for execution by processor 44. Memory 46 may include separate memories for storing instructions and voiding information. In one example embodiment processor 44 and memory 46 may implement loop recorder functionality in which processor 44 overwrites the oldest contents within memory 46 with new data as storage limits are met, thereby conserving data storage resources. Processor 44 may selectively record over the data stored within memory 46, such as signals from sensor 42 that are not indicative of a voiding event. Alternatively, processor 44 and memory 46 may be configured to immediately transmit voiding information to another device, such as patient programmer 16 or clinician programmer 18. In this case, memory, processing, and power consumption overhead in automatic voiding diary 14 can be substantially reduced.

As shown in FIG. 2, therapy delivery device 30 includes therapy delivery module 32, processor 34, telemetry module 36, and memory 38. Automatic voiding diary 14 communicates with therapy delivery device 30 and, more particularly, telemetry module 36 to transmit voiding information to programmers 16 and 18. In particular, automatic voiding diary 14 may communicate with processor 34 which controls telemetry module 36. Processor 34 may control telemetry module 36 to transmit voiding information to an external device, such as patient programmer 16, clinician programmer 18, or other external device, on a continuous basis, at periodic intervals, or upon request from an external device, such as patient programmer 16 or clinician programmer 18.

Telemetry module 36 provides a wireless interface with patient programmer 16 and clinician programmer 18. The wireless interface may be one of wireless telemetry, Bluetooth, IEEE 802.11 (a), (b), (g), or other standard proprietary wireless interfaces.

Therapy delivery device 30 delivers therapy to patient 10 for urinary incontinence via therapy element 15. Therapy element 15 may include electrodes carried on one or more leads, electrodes on the housing of IMD 12, one or more fluid delivery devices, or any combination thereof. Accordingly, therapy delivery module 32 may include an implantable stimulation generator or other stimulation circuitry that delivers electrical signals, e.g., pulses or substantially continuous signals, such as sinusoidal signals, to patient 10 via at least some of the electrodes of therapy element 15 under the control of processor 34.

The stimulation energy generated by therapy delivery module 32 may be formulated as stimulation energy for treatment of any of a variety of urinary or fecal incontinence disorders. Example stimulation therapies include delivering stimulation to nerves, i.e., sacral or pudendal nerves, or directly to a urinary sphincter, where the stimulation causes the urinary sphincter to constrict and retain urine within the bladder. Electrical stimulation may also be directed to other muscles of the pelvic floor because some of these muscles play a role in controlling urinary voiding events.

An exemplary range of electrical stimulation parameters likely to be effective in treating urinary or fecal incontinence, e.g., when applied to the sacral or pudendal nerves, are as follows:

1. Frequency: between approximately 0.5 Hertz (Hz) and approximately 500 Hz, such as between approximately 5 Hz and approximately 250 Hz or such as between approximately 10 Hz and approximately 50 Hz.

2. Amplitude: between approximately 0.1 volts and approximately 50 volts, such as between approximately 0.5 volts and approximately 20 volts or between approximately 1 volt and approximately 10 volts. The amplitude may be representative of a biological load between 10 ohms and approximately 10,000 ohms.

3. Pulse Width: between approximately 10 microseconds and approximately 5000 microseconds, such as between approximately 100 microseconds and approximately 1000 microseconds or between approximately 180 microseconds and 450 approximately microseconds.

Other electrical stimulation parameters may also be useful for managing urinary incontinence.

In embodiments in which one or more fluid delivery devices are part of therapy elements 15, therapy delivery module 32 may include a one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites within patient 10.

Processor 34 controls therapy delivery module 32 to deliver electrical stimulation via a programmable stimulation signal (e.g., in the form of electrical pulses or substantially continuous-time signals) with pulse amplitudes, pulse widths (if applicable), and frequencies (i.e., pulse rates) specified by programs of the parameter set selected from memory 38. Memory 38 may store therapy parameter sets (i.e., therapy programs) that are available to be selected by the patient for delivery of electrical stimulation and/or drug therapy. Memory 38 may also store schedules for delivering therapy to patient 10. Memory 38 may include any combination of volatile, non-volatile, removable, magnetic, optical, or solid state media, such as ROM, RAM, EEPROM, flash memory, or the like.

Processor 34 may also control therapy delivery module to deliver each pulse according to a different program of the parameter set. In some embodiments, processor 34 may control therapy delivery module 32 to deliver a substantially continuous stimulation waveform rather than pulsed stimulation. Additionally, processor 34 may automatically adjust therapy parameters based on voiding information. In this way, voiding information from automatic voiding diary 14 may be used in a closed loop therapy adjustment system implemented by therapy delivery device 30 to adjust one or more therapy parameters with the goal of minimizing the occurrence of any further involuntary incontinence events.

Processor 34 may include a microprocessor, microcontroller, DSP, ASIC, FPGA, discrete logic circuitry, or a combination of such components. Processor 34 is programmed to control delivery of therapy according to a selected parameter set stored in memory 38. Specifically, processor 34 controls therapy delivery module 32 to deliver electrical stimulation, drug therapy, or a combination of both. For example, processor 34 may control which drugs are delivered and the dosage of the drugs delivered or the stimulation parameters with which therapy delivery module 32 delivers electrical stimulation therapy to patient 10.

A power source (not shown) delivers operating power to the components of automatic voiding diary automatic voiding diary 14 and therapy delivery device 30. In embodiments in which automatic voiding diary 14 and therapy delivery device 30 are located within the same housing, the power source may be shared among devices 14 and 30. The power source may take the form of a small, rechargeable or non-rechargeable battery, or an inductive power interface that transcutaneously receives inductively coupled energy. In the case of a rechargeable battery of an implanted device, the power source similarly may include an inductive power interface for transcutaneous transfer of recharge power.

Although FIG. 2 illustrates therapy delivery device 30 and automatic voiding diary automatic voiding diary 14 as being contained within a single housing, it should be understood that therapy delivery device 30 and automatic voiding diary automatic voiding diary 14 may be implemented as separate devices. Thus, FIG. 2 should not be considered limiting of the invention as broadly described in this disclosure in any way. However, by incorporating therapy delivery device 30 and automatic voiding diary automatic voiding diary 14 in a common housing of an IMD (IMD 12), circuitry associated with both devices 14 and 30, such as a processor and memory, may be shared and fabricated on a single circuit board. As a result, the IMD, i.e., IMD 12, may be substantially smaller in size and cost less than separate devices for delivering therapy and storing voiding information. Additionally, IMD 12 may be implanted within patient 10 using fewer incisions and requiring less space than separately implanting therapy delivery and voiding diary devices.

Figure 3:
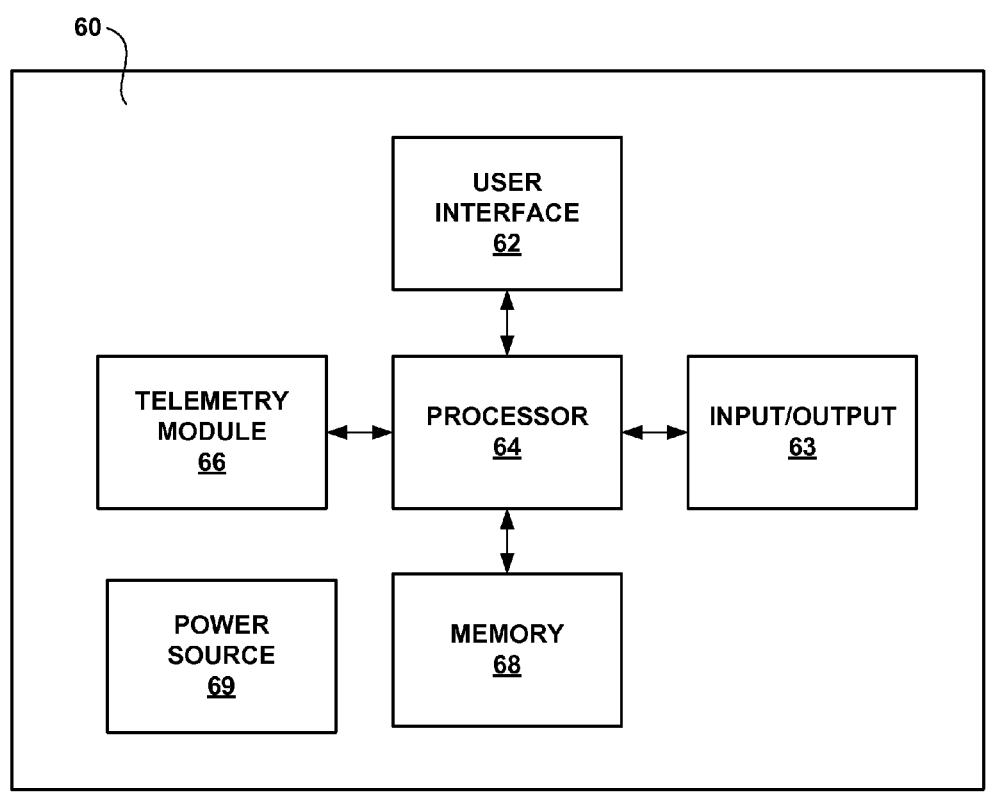
FIG. 3 is a block diagram illustrating components of a programmer associated with the IMD of FIG. 1.

FIG. 3 is a functional block diagram illustrating various components of an external device 60 that may be configured to operate as patient programmer 16 or clinician programmer 18. As shown in FIG. 3, external device 60 includes user interface 62, input/out module 63, processor 64, memory 68, telemetry circuit 66, and power source 69. A clinician or patient 10 may interact with user interface 62 in order to review the voiding log, modify a component of the voiding log, request voiding information from IMD 12, or manually adjust one or more therapy parameters of the stimulation and/or drug therapy. In this way, external device 60 can be viewed as patient programmer 16 or clinician programmer 18.

In general, patient programmer 16 provides limited functionality in comparison with clinician programmer 18. As previously described, patient 10 may interact with a patient programmer 16 to view the voiding log and may be allowed to adjust selected parameters. For example, patient 10 may interact with patient programmer 16 control therapy, e.g., by selecting a program from a limited list of programs or adjusting a parameter within a defined range. Patient 10 may also enter input that identifies a voiding event as a controlled or involuntary event.

In contrast, a clinician may interact with clinician programmer 18 to program therapy in IMD 12, for example, by selecting one or more therapy programs from memory 68. The clinician may also define therapy parameters without being limited to pre-defined ranges. The clinician or patient 10 may also interact with device 60 to receive diagnostic information from IMD 12, such as the remaining life of the power source or electrode impedance measurements if therapy element 15 or the housing of IMD 12 includes one or more sensing or stimulation electrodes.

User interface 62 may include a display and one or more input buttons that allow clinician programmer 18 to receive input from the clinician. The screen may be a liquid crystal display (LCD) or touch screen. The input buttons may include a touch pad, increase and decrease buttons, emergency shut off button, an alphanumeric keypad or a reduced set of keys associated with particular functions or other buttons needed to control the stimulation and/or drug therapy. Processor 64 may present the voiding log via the display of user interface 62 and the clinician may review the voiding log of voiding information to determine an effective treatment or adjust therapy parameters for the currently selected therapy.

Processor 64 may include a microprocessor, microcontroller, DSP, ASIC, FPGA, discrete logic circuitry, or a combination of such components. Processor 64 controls user interface 62, retrieves data from memory 68 and stores data, such as voiding information, within memory 68. Processor 64 also controls the transmission of data through telemetry module 66 to IMD 12. Specifically, processor 64 controls receiving voiding information from automatic voiding diary device 14 and transmission of therapy programs to therapy delivery device 30.

Processor 64 may receive parameter set selections made by patient 10 or a clinician via user interface 62, and may either transmit the selection or the selected parameter set to IMD 12 via telemetry module 60 for delivery of drug therapy and electrical stimulation according to the selected parameter set. Telemetry module 66 includes a transceiver for wireless communication, appropriate ports for wired communication or communication via removable electrical media, or appropriate drives for communication via removable magnetic or optical media. Telemetry module 60 may support both wireless communication with IMD 12 and wireless communication with another programmer or external device.

In some embodiments, external device 60 may include input/output module 63 in addition telemetry module 66. Input/output module 63 allows processor 64 to communicate with another programmer. For example, where external device 60 stores parameter sets in memory 68, processor 64 may receive parameter sets from another programmer via input/output module 63 during programming by a clinician.

Memory 68 may include any combination of volatile, non-volatile, removable, magnetic, optical, or solid state media, such as ROM, RAM, EEPROM, flash memory, or the like. Memory 68 includes operation instructions for processor 64 and voiding information. In embodiments, where therapy is also delivered, memory 68 may also store therapy parameters to define the therapy. Memory 68 may also include a history of all user inputs and changes to the voiding information for later review if necessary. In addition, memory 68 may store voiding information received from automatic voiding diary 14 (FIG. 2).

Telemetry module 66 allows the transfer of data to and from IMD 12. Telemetry circuit 66 may receive voiding information automatically from automatic voiding diary device 14 as voiding events are detected, at a scheduled time, when memory within IMD 12 is full, or when requested by a clinician through user interface 62. Power source 69 may be a rechargeable battery, such as a lithium ion or nickel metal hydride battery. Other rechargeable or conventional, nonrechargeable batteries may also be used. In some cases, clinician programmer 18 may be powered by a connection to an alternating current outlet.

Figure 4:
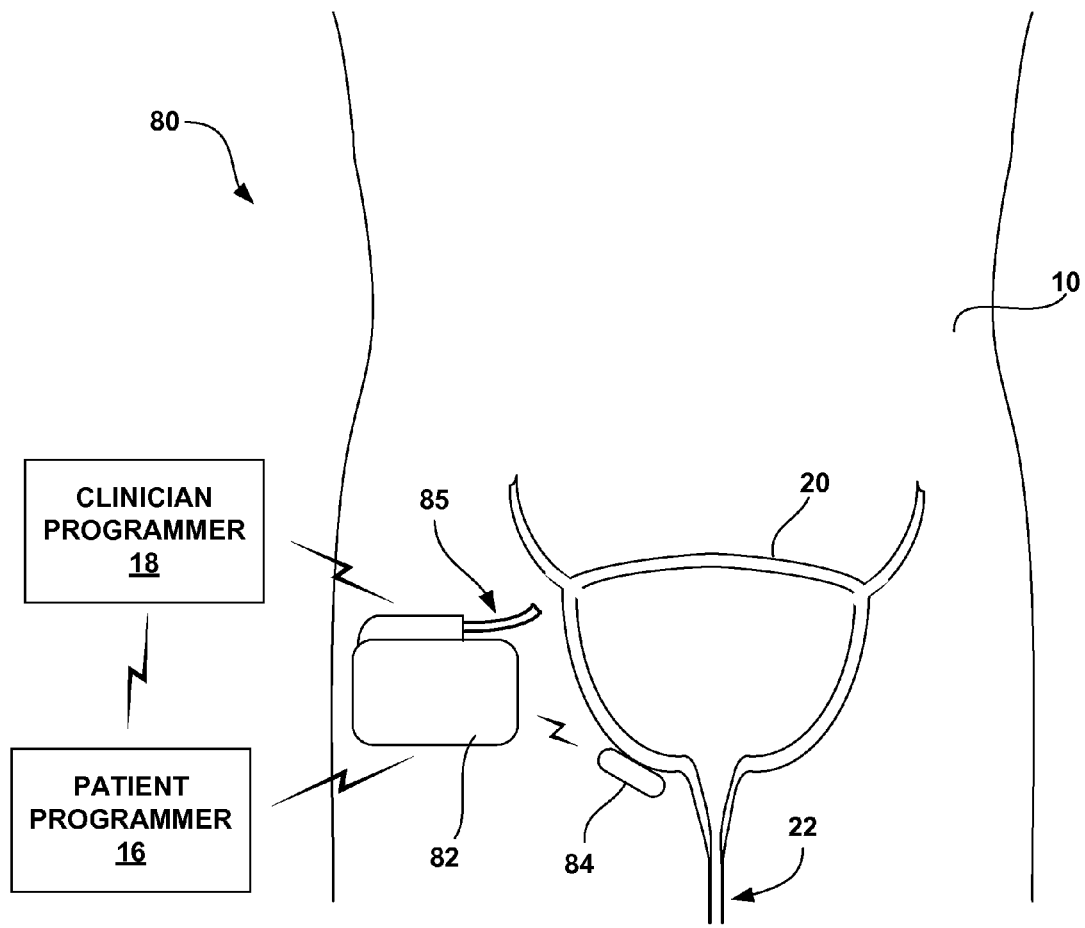
FIG. 4 is a schematic diagram illustrating a system that includes separate devices implanted within a patient, where the devices are configured to deliver therapy to treat urinary incontinence and operate as an automatic voiding diary.

FIG. 4 is a schematic diagram illustrating a system 80 including a therapy delivery device 82 that delivers therapy to patient 10 for treating urinary incontinence and an implantable automatic voiding diary 84. As shown in FIG. 4, therapy delivery device 82 and automatic voiding diary device 84 are separate IMDs that wirelessly communicate with one another. Alternatively, therapy delivery device 82 and implantable automatic voiding diary 84 may be coupled via a wired connection (e.g., a conductor electrically coupling therapy delivery device 82 to implantable automatic voiding diary 84). With respect to FIG. 4, therapy delivery device 82 and automatic voiding diary 84 are substantially similar to therapy delivery device 30 and automatic voiding diary 14, respectively, of FIG. 1. Consequently, system 80 operates in substantially the same manner as system 2 shown in FIG. 1.

In one embodiment, automatic voiding diary 84 includes a microphone (not shown) that generates an electrical signal based on a sound associated with a voiding event and a memory that stores voiding information for detected voiding events. Therefore, it should be understood that automatic voiding diary 84 generally operates in similar fashion as automatic voiding diary 14 in FIGS. 2 and 3. For this reason, the details of operation of device 84 are not described in detail to avoid redundancy in this disclosure.

In the illustrated example of FIG. 4, therapy delivery device 82 may be implemented as an INS, drug pump, or other therapy delivery device well known in the field of IMDs for delivering stimulation therapy, drug therapy, or a combination of both. Additionally, similar to therapy elements 15, therapy element 85 is coupled to therapy delivery device 82 and may represent a lead carrying one or more electrodes that delivery stimulation in the form of electrical pulses or a fluid delivery device, such as a catheter, that delivers one or more drugs. Although only one therapy element for therapy delivery device 82 is illustrated in FIG. 4, in some embodiments, therapy delivery device 82 may include more than one therapy element 85. For example, in some embodiments, system 80 may include more than one lead that each carry electrodes for delivering stimulation therapy, more than one catheter that each deliver one or more drugs, or any combination thereof. Additionally, therapy element 85 may, in some embodiments, carry electrodes and deliver drugs for treating urinary incontinence.

With respect automatic voiding diary device 84, however, device 84 may be configured to have a capsule-like shape. That is, the housing of device 84 may have the shape of a rounded capsule and may have a length of approximately 2 centimeters (cm) to approximately 5 cm, a width of approximately 1.5 cm to approximately 5 cm, and a thickness of approximately 0.5 cm to approximately 2.5 cm. Alternatively, the capsule-like shape may exhibit a circular cross-section, in which device 84 may have a diameter of approximately 0.5 cm to 1.5 cm, rather than width and height dimensions. The shape and size of device 84 may facilitate implantation at locations within patient 10 that promote sensing of sounds associated with a voiding event. Accordingly, in an example embodiment, voiding diary device 84 may be configured to be percutaneously introduced into patient 10. In such an embodiment, the size and shape of voiding diary device 84 enables it to be introduced using an introducer device, such as a needle.

Although not shown in FIG. 4, the microphone used by automatic voiding diary device 84 may be located on or within the housing of device 84. Alternatively, the microphone may be carried on a lead (not shown) that extends from the housing of device 84. The microphone may be located medially along the length of the lead or may be located at the distal end of the lead. As previously described, positioning the microphone at the distal end of the lead may enable the microphone to be implanted at a particular site within patient 10 that results in an improved quality of signal generated by the microphone.

In any case, automatic voiding diary device 84 operates as a wireless sensor that is configured to transmit voiding information to therapy delivery device 82 in addition to or instead of transmitting voiding information to patient and clinician programmers 16 and 18. For example, therapy delivery device 82 may control or adjust therapy parameters based on voiding information received from automatic voiding diary device 84. In another example, although not explicitly shown in FIG. 4, automatic voiding diary device 14 may wirelessly transmit voiding information to patient and clinician programmers 16 and 18 for diagnostic purposes. That is, a patient or clinician may use programmers 16 and 18 to view voiding information received from automatic voiding diary as previously described. Thus, automatic voiding diary 14 may be implanted within patient 10 to generate voiding information for the purposes of patient diagnosis both alone or in combination with therapy delivery device 82.

System 80 may exhibit certain advantages. For example, therapy delivery device 82 and automatic voiding diary 84 may be implanted at different locations within patient 10. For example, therapy delivery device 82 may be implanted in a subcutaneous pocket in the lower back or abdomen of patient 10 whereas automatic voiding diary device 84 may be implanted proximate to bladder 20, urinary tract 22, or other location proximate to the urinary system of patient 10. Alternatively, therapy delivery device 82 may be implanted in a subcutaneous pocket in the lower back or abdomen of patient 10 whereas automatic voiding diary device 84 may be implanted proximate to a portion of the intestines, rectum, or other location proximate to the gastrointestinal tract of patient 10. Implanting automatic voiding diary device 84 at a location proximate to bladder 20, as shown in FIG. 4, may increase the likelihood and reliability of detecting a voiding event based on the electrical signal generated by the microphone of device 84. That is, by implanting device 84 at a location different than that of device 82, the electrical signal generated by the microphone of device 84 may have improved quality. In other words, the electrical signal generated by the microphone may be closer to the source of the sounds associated with a voiding event and, at the same time, exposed to a lesser amount of unwanted noise.

Figure 5:
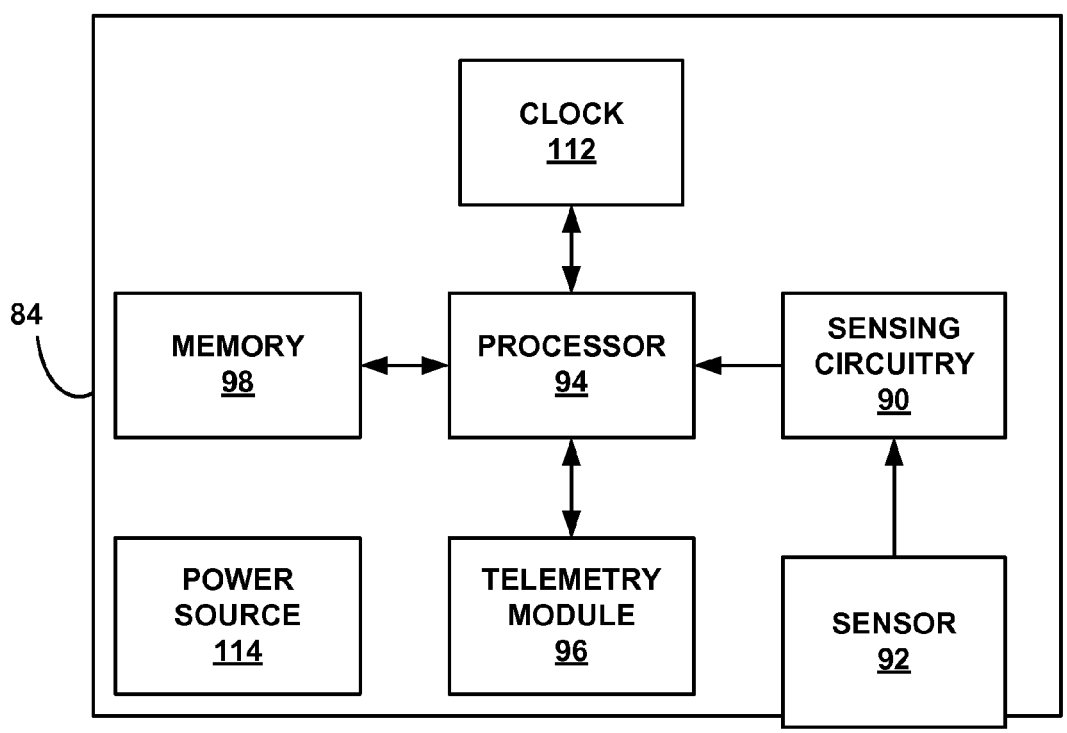
FIG. 5 is a block diagram illustrating components of the automatic voiding diary device in FIG. 4.

FIG. 5 is a block diagram illustrating various components of automatic voiding diary 84. In the illustrated example of FIG. 5, device 84 includes sensing circuitry 90, sensor 92, processor 90, telemetry module 96, memory 98, clock 112, and power source 114. Sensing circuitry 90, sensor 92, processor 94, telemetry module 96, memory 98, and clock 112 are substantially similar to sensor 42, sensing circuitry 40, processor 44, telemetry module 36, memory 46, and clock 48, respectively.

Accordingly, sensor 42 may be a microphone, such as a crystal microphone, condenser microphone, a ribbon microphone, or other type of microphone suitable for implantation within patient 10 that generates an electrical signal based on a sound associated with a voiding event, as previously described. Sensing circuitry 90 generally processes this electrical signal to detect voiding events and memory 98 stores the voiding information under the control of processor 94. Processor 94 may also generate timestamps, information that identifies detected voiding events as voluntary or involuntary events, and other information associated with detected voiding events. As previously described, processor 94 may generate a timestamp based on a clock signal received from clock 112.

In response to detecting a voiding event, processor 94 may store in memory 98 the raw output of sensor 92, the processed signal that is produced by sensing circuitry 90, or data that simply indicates that a voiding event was detected. In addition, processor 94 may also associate and store a timestamp with the voiding information stored in memory 98 based on a clock signal received from clock 112. Further, processor 94 may also store as part of the voiding information associated with a detected voiding event, data that identifies the detected event as a controlled or involuntary event. In this case, processor 94 may generate this data based on a signal received from input mechanism 110. Processor 94 and memory 98 may implement loop recorder functionality or may be configured to transmit voiding information to device 82 or an external device, such as patient or clinician programmers 16 and 18.

Telemetry module 96 may transmit voiding information to an external device in accordance with wireless telemetry protocols, Bluetooth, IEEE 802.11 (a), (b), (g), or other standard proprietary wireless protocols. Telemetry module 96 may also receive information from an external device. For example, telemetry module 96 may receive updated signal models or templates to use for detecting a voiding signature in the signal output by sensor 92.

Figure 6:
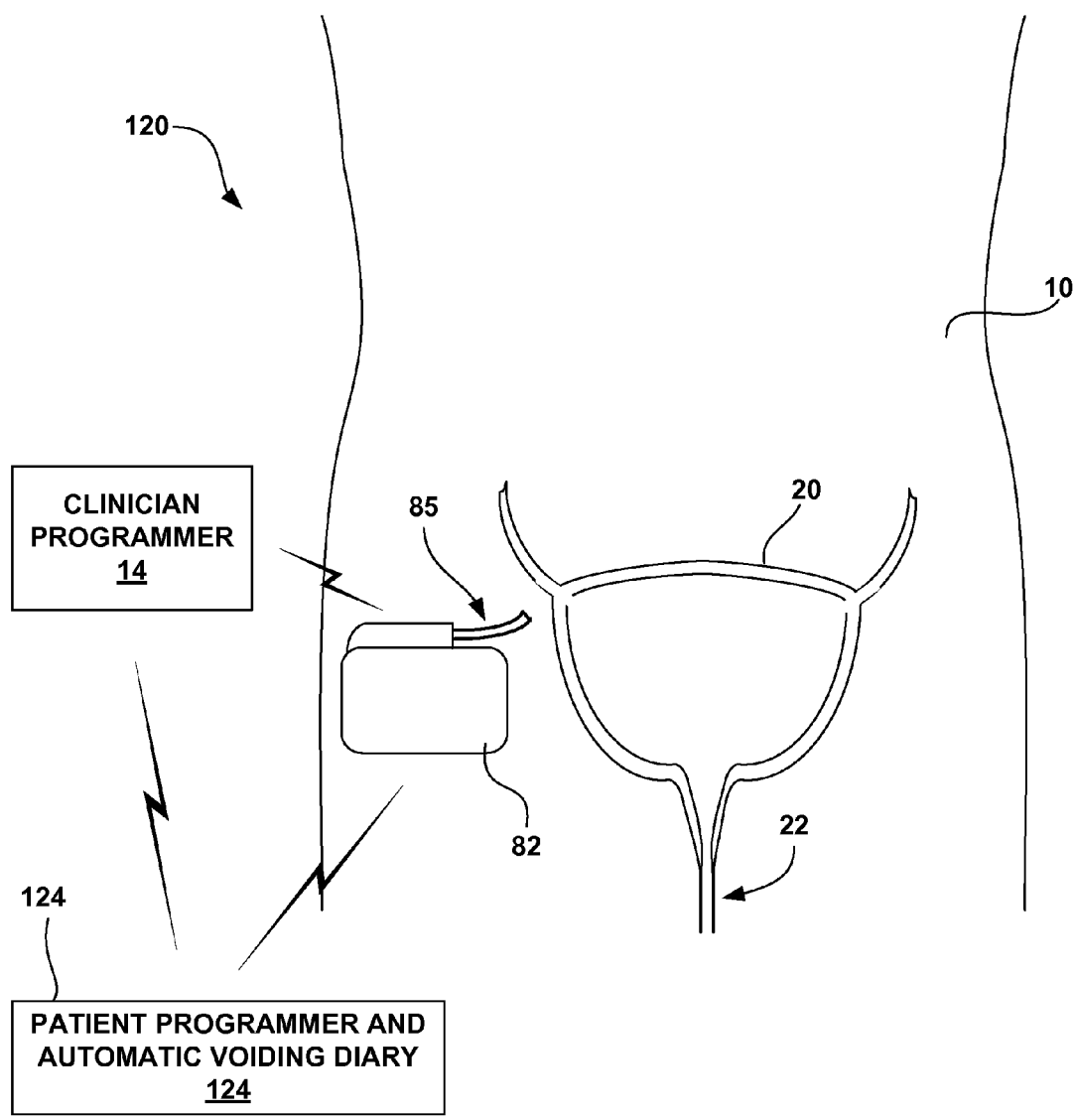
FIG. 6 is a schematic diagram illustrating a system including an embodiment of an external device configured to operate as an automatic voiding diary.

FIG. 6 is a schematic diagram illustrating a system 120 that includes therapy delivery device 82 and patient programmer and automatic voiding diary 124, which is referred to hereafter as device 124. In general, system 120 operates in a similar fashion as systems 2 and 80 in FIGS. 1 and 4, respectively, but provides an automatic voiding diary as an external device instead of a device implanted within patient 10. In particular, therapy delivery device 82 in FIG. 6 corresponds to therapy delivery device 82 illustrated in FIG. 4 and delivers therapy to patient 10 for urinary or fecal incontinence. Device 124, however, is configured to operate similar to patient programmer 16 and include the functionality of automatic voiding diary 14 and 84. That is, device 124 operates as an automatic voiding diary as well as a patient programmer as previously described in this disclosure.

Device 124 includes a microphone that may be positioned on or within the housing of device 124. Since device 124 is an external device, patient 10 may carry device 124 throughout the course of a day. Microphone incorporated in device 124 is positioned external to patient 10, and thus, may be unlikely to detect or generate an electrical signal indicative of internal sounds associated with a voiding event, such as sounds produced by bladder 20, urinary tract 22, rectum (not shown), intestines (not shown), or other organs and tissue (not shown) that produce a sound associated with a urinary or fecal voiding event. However, the microphone incorporated within device 124 may pick up, i.e., generate an electrical signal based on, external sounds associated with a voiding event. These sounds may include but are not limited to a sound produced by urine or feces being voided into a toilet, a toilet flushing, fluid exiting urinary tract 22, fluid or feces being voided into an undergarment, a voice command, or other sound produced by patient 10 or the environment that is associated with a urinary or fecal voiding event.

Device 124 may have the shape and size of a personal electronic device. For example, device 124 may be described as a handheld electronic device that is sized to be held in one hand and can easily be carried in the pocket of a user. Device 124 may or may not include a LCD screen for displaying a user interface with which the user can interact to view voiding information or perform limited programming functions, such as adjust therapy parameters within a pre-defined range of values. Generally, the size of device 124 may not be substantially larger than the size or patient programmer 16. This is because few components are needed to add the functionality provided by automatic voiding diary device 14, i.e., to add the functionality of an automatic voiding diary.

Generally, patient 10 carries device 124 throughout the day. However, unlike patient programmer 16, it may be particularly important to carry device 124 close to the body of patient 10. This is because the distance between device 124 and, more particularly, the microphone carried by device 124, and the body of patient 10 may affect the performance, i.e., the ability of device 124 to detect voiding events. For this reason, it may be advantageous to attach device 124 to the clothing of patient 10 or directly to patient 10 to reduce the distance between the source of the sound and the microphone. This may also minimize the possibility of patient 10 forgetting device 124 at home or at other places, and decreases any burden to patient 10 to carry patient programmer and automatic voiding diary device 124.

In order to increase the likelihood of reliably detecting sounds associated with a voiding event, device 124 may include elements for attaching patient programmer and automatic voiding diary 124 to the clothing of patient 10. Example elements may include clips, pins, bands, adhesives such as tape or Velcro, and the like. As an example, device 124 may include a clip, pin, or band for attaching device 124 to the waist band of pants or shorts.

As shown in FIG. 6, patient programmer and automatic voiding diary 124 wirelessly communicates with clinician programmer 18 and therapy delivery device 82. Accordingly, patient programmer and automatic voiding diary 124 includes the communication features previously described with respect to patient programmer 16 and device 14. For example, device 124 may transmit voiding information to clinician programmer 18 for review by a clinician. Therapy delivery device 82 may also receive voiding information from device 124 for adjusting therapy parameters.

In this way, device 124 automatically tracks voiding events and can be used by patient 10 to review voiding information or provide other input, such as input indicating a voiding event was voluntary or involuntary. Automatically recording voiding events eliminates the need for patient 10 to manually track voiding events, e.g., by entering events in a written or electronic diary. In embodiments in which patient 10 uses device 124 to review voiding information, device 124 includes a display, such as an LCD screen, for presenting the voiding information to patient 10 as a voiding diary. Patient 10 may also be able to confirm that an event was detected correctly prior to the event being written to the diary. Device 124 may also enables patient 10 to enter additional information associated with the voiding event. As an example, patient 10 may interact with device 124, e.g., by depressing one or more buttons, selecting an item from a menu, or the like, to identify a voiding event as a controlled or involuntary event. Thus, device 124 combines the operational features of patient programmer 16 and automatic voiding diary 14 without substantially increasing the size of patient programmer 16.

It should be understood that the operational features of automatic voiding diary 14 and 84 may also be implemented in handheld electronic devices other than a patient programmer. For example, a personal digital assistant (PDA), cell phone, watch, or personal electronic device may be configured to operate as an automatic voiding diary. In such examples, however, patient 10 may also carry a patient programmer, although the automatic voiding diary may be useful without a patient programmer.

Figure 7:
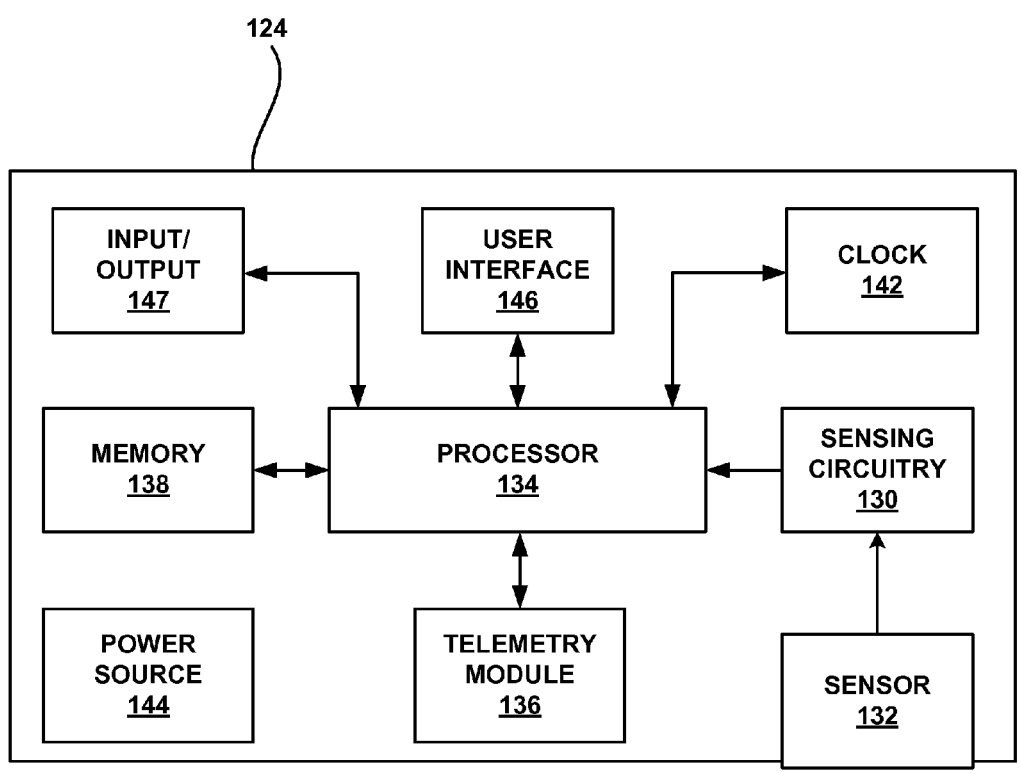
FIG. 7 is a block diagram illustrating components of the external device of FIG. 6.

FIG. 7 is a block diagram illustrating various components of device 124. As described with respect to FIG. 6, device 124 combines the operational features of patient programmer 16 and an automatic voiding diary, such as automatic voiding diary 14 or 84. Accordingly, device 124 includes similar components to patient programmer 16 and device 14.

In the illustrated example of FIG. 7, patient programmer 124 includes sensing circuitry 130, sensor 132, processor 134, telemetry module 136, memory 138, clock 142, power source 144, user interface 146, and input/output module 147. With respect to FIG. 5, sensor 132, sensing circuitry 130, processor 134, telemetry module 136, memory 138, clock 142, and power source 144 correspond to sensor 92, sensing circuitry 90, processor 94, telemetry module 96, memory 98, clock 112, and power source 114, respectively. In addition, processor 134, telemetry module 136, memory 138, and user interface 146 and input/output 147 correspond to processor 64, telemetry module 66, memory 68, user interface 62 and input/output module 63 of FIG. 3, respectively.

Figure 8:
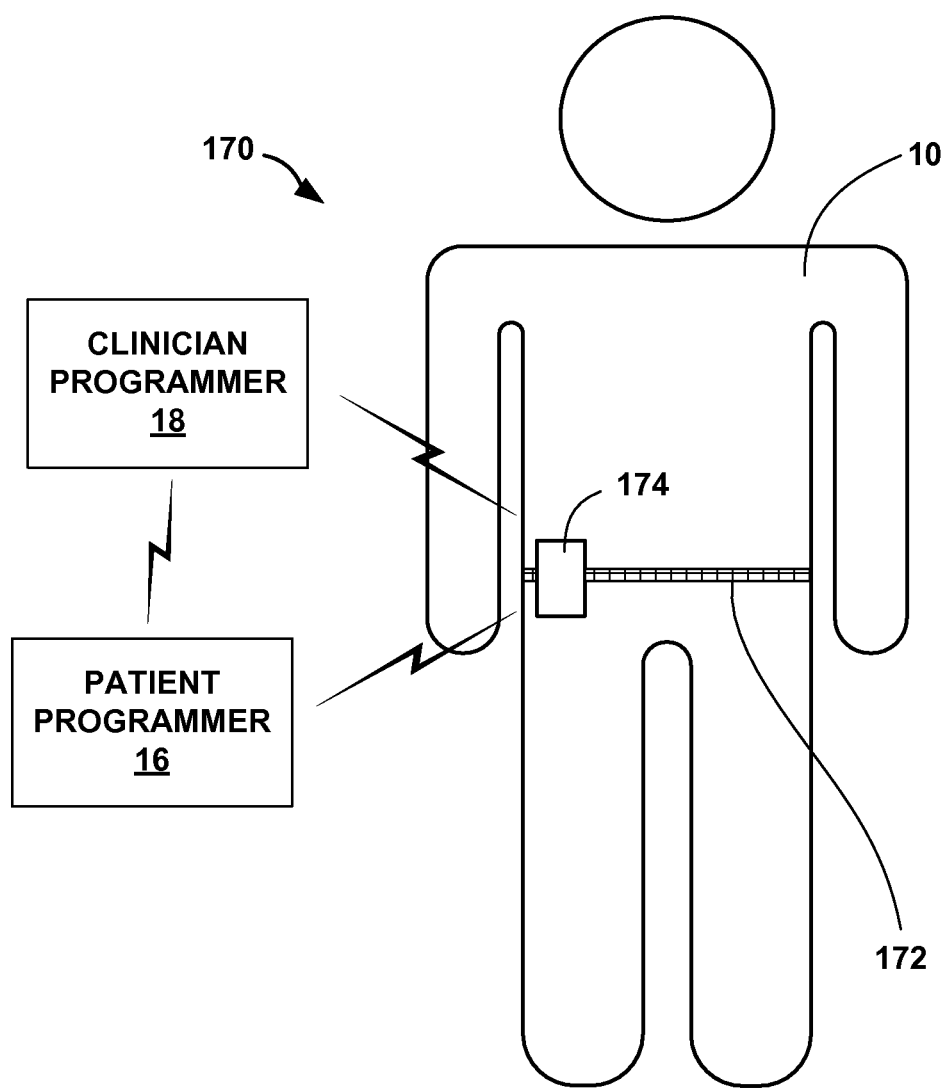
FIG. 8 is a conceptual diagram illustrating a system including another embodiment of an external device configured to operate as an automatic voiding diary.

FIG. 8 is a conceptual diagram illustrating a system 170 including an external device 174 configured to operate as an automatic voiding diary. In FIG. 8, device 174 may generally be configured to be easily carried or worn by patient 10. For example, device 174 may be attached to or otherwise carried by a belt 172 as shown in FIG. 8. Thus, device 174 may have a reduced size that facilitates the discrete attachment to the body or clothing of patient 10.

Similar to the previously described automatic voiding diary devices, device 174 includes a microphone (not shown) that generates an electrical signal based on sounds associated with voiding events. The microphone may be positioned on or within the housing of device 174. Device 174 generally does not include features, such as an interface, for displaying voiding information to patient 10 or receiving input from patient 10. Rather, device 174 wirelessly transmits recorded voiding information to one or both of patient and clinician programmers 16 and 18. Accordingly, device 174 may be viewed as providing similar operational features as automatic voiding diary devices 14 and 84.

However, in contrast to devices 14 and 84, device 174 is not implanted within the body of patient 10. Consequently, device 174 may be particularly useful for patients that are not good candidates for implantable medical devices. Device 174 may also be useful as a preliminary diagnostic device to determine if a patient would benefit from an implantable automatic voiding diary device and/or implantable therapy delivery device. Furthermore, device 174 may also be useful during a trialing period (or a "calibration mode") in which external sounds associated with voiding, or voiding characteristics of the electrical signal generated by the microphone within device 174 are determined. The external sounds may differ, depending on the life style of patient 10, and different patients may generate different external sounds or be subjected to different environmental sounds during voiding events. Accordingly, device 174 may be used to "train" the processor within device 174 or another computing device to recognize certain sounds or electrical signals as indicative of a voiding event.

It is important that device 174 be attached to the body or clothing of patient 10 to increase the likelihood of reliably detecting sounds associated with a voiding event. For this reason, device 174 may include elements for attaching device 124 to the clothing or body of patient 10. As examples, device 174 may include a clip, pin, or band for attaching device 174 to the waist band of pants or shorts. As another example, device 174 may include a strip of Velcro that attaches to a corresponding strip of Velcro on an undergarment. In this example, the Velcro may be strategically positioned, e.g., near the groin region of patient 10. In this way, device 174 may be more likely to detect sounds associated with a voiding event.

Placement of device 174 near an undergarment may be particularly advantageous for detecting involuntary events in which fluid is voided into the undergarment. That is, the sound of fluid being voided into an undergarment may be difficult to detect with an external or internal device because of the reduced volume of sound in comparison to other sounds (such as the sound produced by flushing a toilet), and accordingly, positioning the microphone to the source of the sound may increase the possibility of the microphone capturing sounds of fluid being voided into an undergarment. By attaching device 174 to the undergarment at a location proximate to the opening of the urethra of patient 10, the distance between the source of the sound and device 174 is reduced. Additionally, device 174 may also be able to detect other noises, such as sounds produced by fluid being voided into a toilet or the sound produced by a toilet flushing, at this location.

Figure 9:
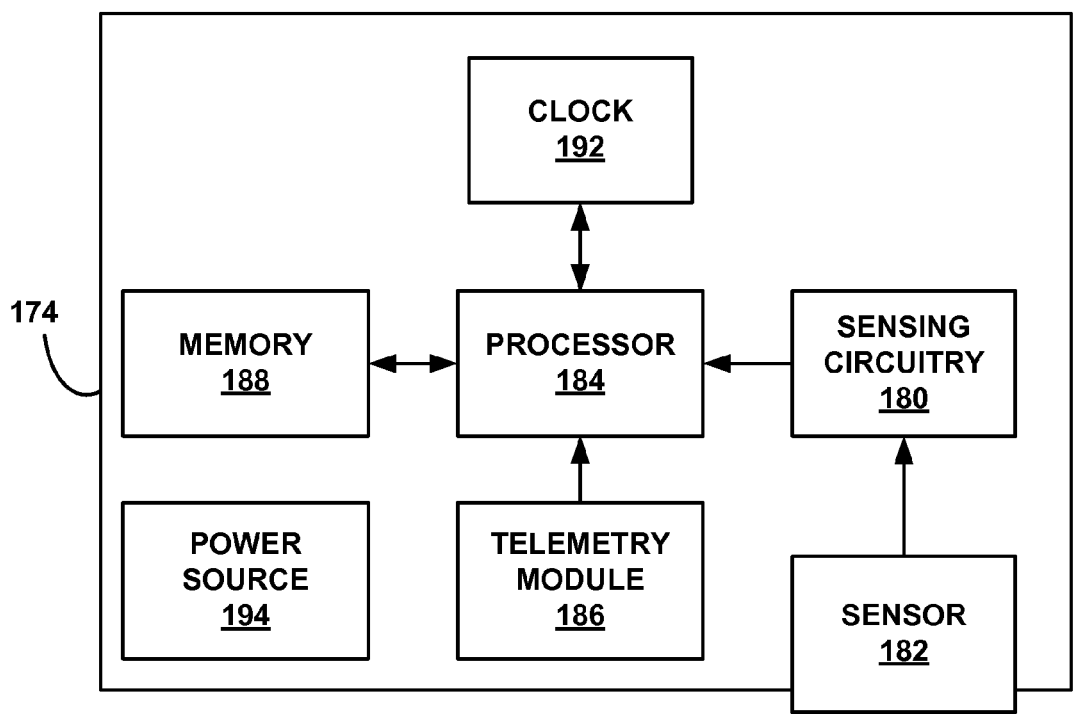
FIG. 9 is block diagram illustrating components of the example external device in FIG. 8.

FIG. 9 is a block diagram illustrating various components of device 174. In the illustrated example of FIG. 9 device 174 includes sensing circuitry 180, sensor 182, processor 184, telemetry module 186, memory 188, clock 192, and power source 194. These components are substantially similar to sensor 92, sensing circuitry 90, processor 90, telemetry module 96, memory 98, clock 112, and power source 114, respectively, of automatic voiding diary 84 of FIG. 5.

Figure 10:
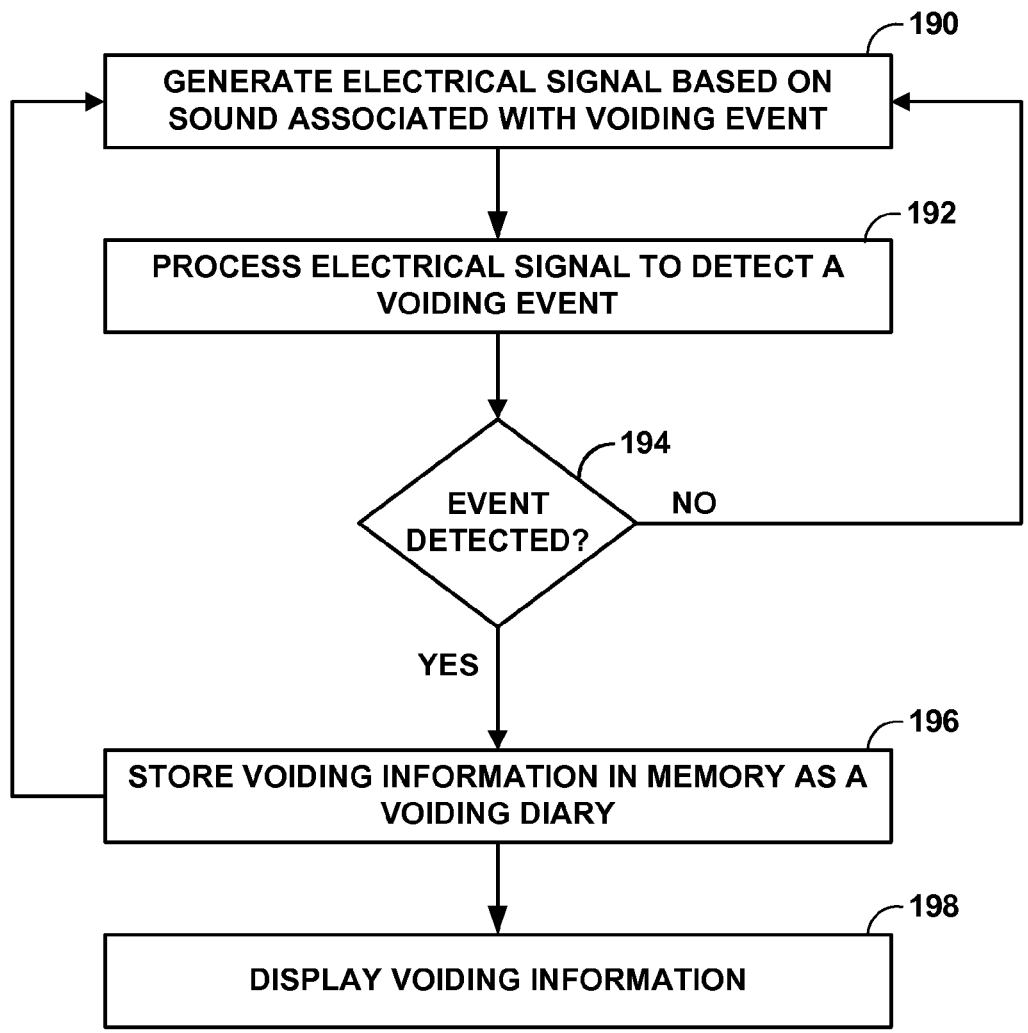
FIG. 10 is a flow diagram illustrating an example technique for automatically detecting voiding events and recording voiding information for the detected voiding events.

FIG. 10 is a flow diagram illustrating an example technique for automatically detecting voiding events via a microphone, and recording voiding information for the detected voiding events. The example technique may be employed by any of previously described devices 14, 84, 124 and 174. Although various devices have been described in this disclosure for generating a voiding diary, FIG. 10 will be described with respect to automatic voiding diary device 14. It should be understood, however, that the flow diagram of FIG. 10 may also be used to describe the operation of other automatic voiding diary devices that generate a signal indicative of a sound associated with a voiding event, such as devices 84, 124, and 174.

The technique begins with device 14 and, more particularly, the microphone associated with device 14 generating an electrical signal based on sounds associated with voiding events (190). As previously described, a sound associated with a voiding event may be an internal or external noise that can be translated into an electrical signal by a microphone. Internal sounds may includes sounds produced by bladder 20, urinary tract 22, rectum (not shown), intestines (not shown), or other organs and tissue (not shown) of patient 10 that produce a sound associated with a urinary or fecal voiding event. External sounds may be sounds produced by patient 10 or the environment during a voiding event, such as a sound produced by urine or feces being voided into a toilet, a toilet flushing, fluid exiting urinary tract 22, urine or feces being voided into an undergarment, a voice command, or other sound associated with a urinary or fecal voiding event.

Generally, device 14 generates an electrical signal substantially continuously. Thus, only portions of the electrical signal generated by sensor 92 include a voiding signature. For this reason, device 14 processes the electrical signal to detect a voiding event (192). As previously described, processing the signal may involve comparing the signal to a signal template stored in memory. Processing the signal may further involve processing the signal to remove unwanted signal components and utilizing low power detection techniques, as previously described.

In some embodiments, device 14 does not generate the electrical signal substantially continuously, but may enter a sleep state in which device 14 does not generate the signal if an amplitude the signal remains below a threshold value for a threshold amount of time, thus indicating that patient 10 is sleeping or otherwise not likely to void. The sleep state may help conserve energy. During the sleep state, device 14 may only generate the signal periodically, such as about every second, about every minute, or about every hour. Device 14 may be "awoken" from the sleep state and enter an active state upon detecting a sound (via the electrical signal) that is above an awake threshold. The sleep thresholds and awake thresholds may be determined by a clinician or a manufacturer of device 14. Alternatively, device 14 may include an accelerometer or another device configured to detect patient movement, where the accelerometer generates a signal which causes device 14 to "wake up" from the sleep state. The accelerometer may generate the "awaken" signal in response to detecting motion during the night hours or detecting motion after extended periods of time of inactivity.

In some cases, device 14 may be used to detect voiding events during a sleep state (e.g., to diagnose nocturia). In such cases, the clinician may program device 14 to not enter the sleep state.

After processing the signal, device 14 determines if a voiding event has been detected (194). In the event that a voiding event has not been detected ("NO" branch of decision block 194), device 14 generates a signal based on detected sounds (190) and processes the signals to detect a voiding event (192). In this way, steps 190, 192, and 194 form a loop that executes until a voiding event is detected ("YES" branch of decision block 194).

In response to detecting a voiding event, device 14 stores voiding information (196). The voiding information may include a portion of the electrical signal that includes a voiding signature, data that indicates a detected voiding event, a timestamp associated with a detected voiding event, and data that identifies the voiding event as a voluntary or involuntary event. The voiding information may be stored in local memory or transmitted to an external device, such as patient or clinician programmers 16 and 18, to be stored. After recording the voiding information in memory 46 (FIG. 2), device 14 may continue generating the electrical signal based on detected sounds (190), and so forth.

The voiding information stored within memory 46 may be displayed to the patient or a clinician via programmers 16 and 18, respectively (198). The patient may review the information to verify that the information is correct. A clinician may review the information to monitor and diagnose a condition of the patient and to adjust therapy parameters.

Figure 11:
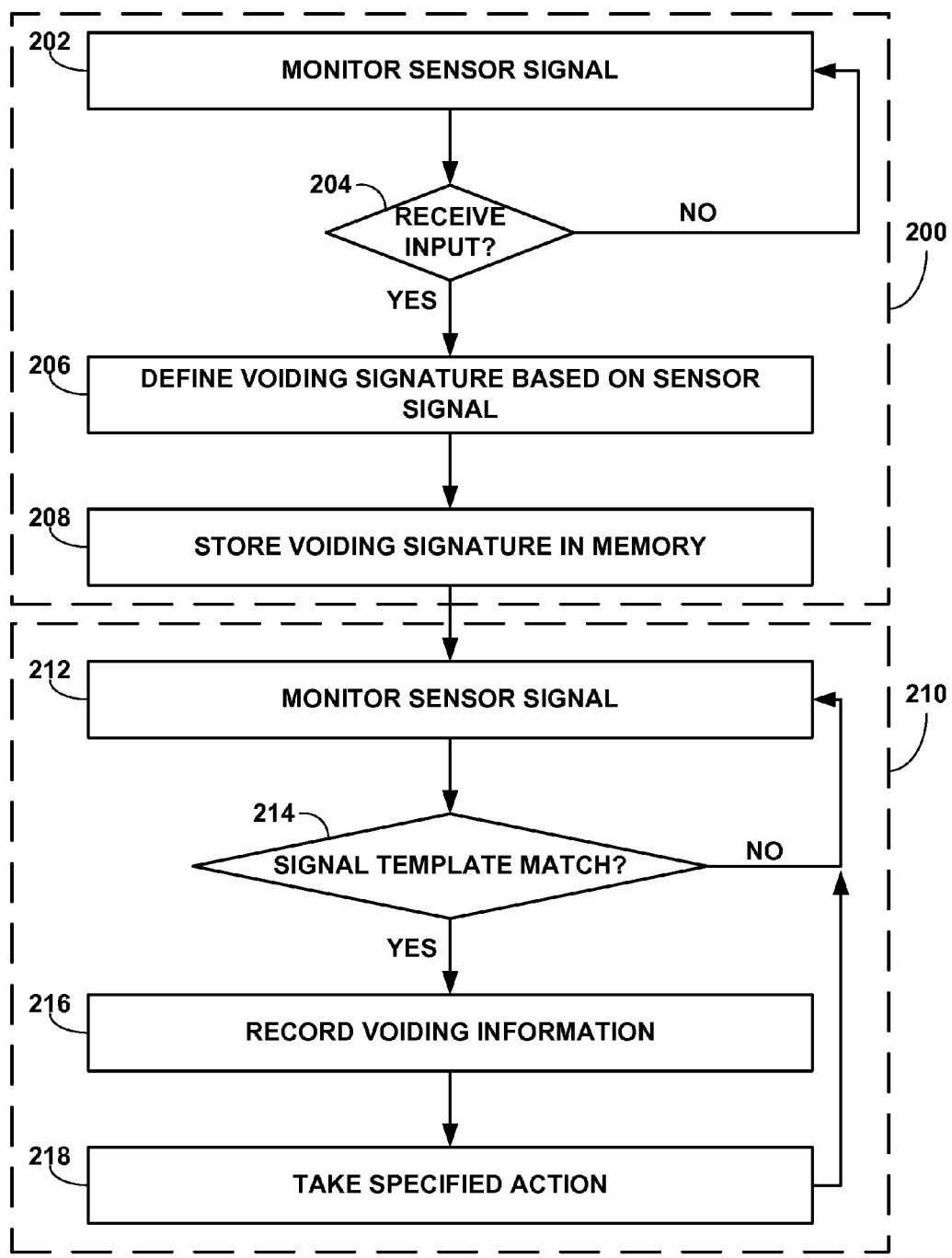
FIG. 11 is a flow diagram illustrating an example technique for calibrating an automatic voiding diary device in accordance with an embodiment of the invention.

FIG. 11 is a flow diagram illustrating an example technique for calibrating an automatic voiding diary to detect voiding events. Similar to the flow diagram illustrated in FIG. 10, the example technique in FIG. 11 is described with respect to automatic voiding diary 14 (device 14), but may be employed by any of the previously described devices including a microphone for generating a signal indicative of detected sounds, i.e., devices 84, 124, and 174.

In particular, FIG. 11 shows a calibration mode 200 and an operational mode 210. In the calibration mode, a sensor signal, i.e., an electrical signal generated by the microphone associated with device 14, is monitored (202). The sensor signal is monitored in a controlled environment. For example, patient 10 may be given fluids to drink for a period of time to induce a natural voiding event. Alternatively, a clinician may actively fill the bladder via a catheter to induce or simulate an actual voiding event.

As yet another alternative, if device 14 is configured to generate a signal indicative of external sounds, the calibration mode 200 in which device 14 "learns" which sounds are associated with voiding events may be conducted outside of the clinician's office. As previously discussed, the external sounds associated with voiding events may differ based on the patient.

As the sensor signal is monitored, patient 10 provides input when the voiding event occurs (204). When input is not received, steps 202 and 204 are repeated, i.e., the process continues to monitor the received sensor signal for received patient or clinician input.

When input is received ("YES" branch of decision block 204), device 14 defines a voiding signature based on the electrical signal (206). Defining the voiding signature may involve storing a waveform of that particular portion of the electrical signal in memory (208) as a voiding signature template for correlation with subsequently received signals to identify voiding events. The voiding signature may include one or more characteristics of the sensor signal, such as amplitude, frequency, time intervals, morphology, or the like.

Upon defining the voiding signature, device 14 may be used in an operational mode 210 to detecting voiding events. For example, in one embodiment, device 14 monitors the sensor signal received from the microphone (212) of device 14 and compares the sensor signal to the stored signal template to determine whether there is a substantial signal template match (214). If there is not a match, the sensor signal continues to be monitored. If a signal template match is detected ("YES" branch of decision block 214), however, device 14 records voiding information (216) and, in some embodiments, takes a specified action (218). The specified action may be, for example, transmitting the voiding information to an external programmer or adjusting therapy parameters based on the voiding information.

Figure 12:
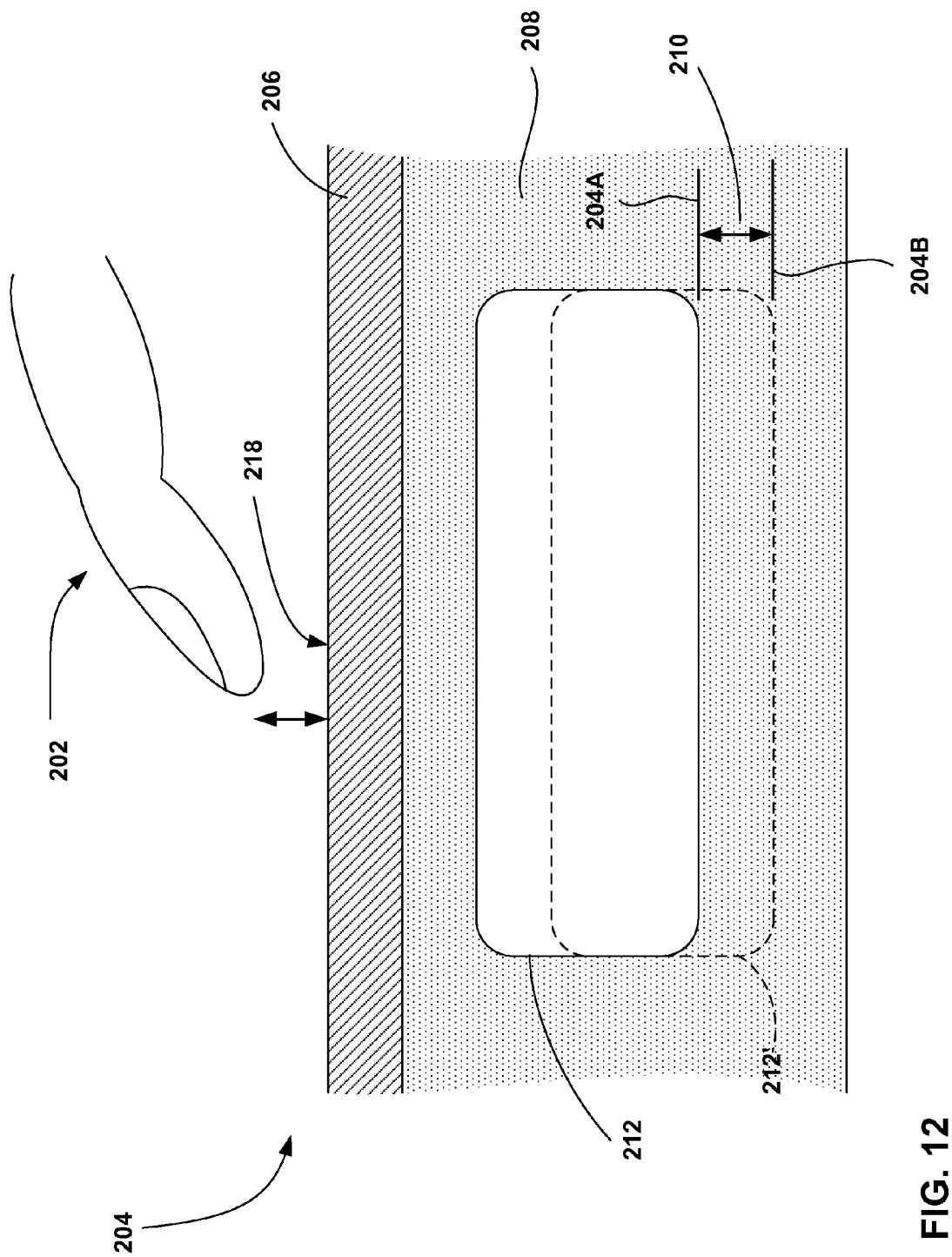
FIG. 12 is a schematic diagram illustrating an example IMD that records voiding information based on a patient defined action.

FIG. 12 is a conceptual cross-sectional view of an abdominal region 204 of a patient, such as patient 10. Abdominal region 204 includes epidermis 206 and subcutaneous tissue 208. FIG. 12 further shows a device 212 implanted within subcutaneous tissue 208. In general, device 212 may operate similar to previously described automatic voiding diary devices 14 and 84, but includes additional features for providing a user friendly and accurate implantable automatic voiding diary device. Alternatively, device 212 may detect urinary or fecal voiding events using other techniques known in the art. For example, device 212 may detect urinary voiding events using one or more pressure sensors, flow sensors, strain gauges, sensing electrodes, or other types of sensors used for detecting urinary voiding events and detect fecal voiding events using one or more pressure sensors, strain gauges, sensing electrodes, such as electromyography sensors for detecting detrusor or bowel muscle contraction, or other types of sensors used for detecting fecal voiding events. In any case, when device 212 detects a voiding event or receives a signal from another device that detects voiding events, device 212 records voiding information in response to receiving a patient defined action. The voiding information may be information that identifies a detected voiding event as a voluntary or involuntary event. In FIG. 12, the patient defined action is the "tapping" of finger 202 on skin 218 located above or superior to device 212.

Because device 212 operates similar to the previously described automatic voiding diary devices, these common features are not described in detail with respect to FIG. 12.

Rather, the purpose of FIG. 12 is to describe the additional features of device 212. Unlike the previously described automatic voiding diary devices, device 212 includes an input mechanism that generates an electrical signal based on the patient defined action, i.e., tapping. This signal is processed and associated with a detected voiding event (e.g., detected via a microphone within device 212) to generate data that identifies a detected voiding event as a voluntary or involuntary event. This data is also referred to as "identification information" in this disclosure and may be stored in memory of device 212, or an external device, as part of the voiding information that forms the voiding diary.

Identification information may be useful for diagnosing the condition of patient 10 and determining the efficacy of therapy that is delivered to the patient. For example, determining the number of incontinence events and/or the ratio of incontinence events to involuntary events may be critical to accurately diagnose the patient and determine the efficacy of therapy. In addition, the identification information may be used in a closed-loop therapy adjustment system to adjust one or more therapy parameters. For example, if the identification information identifies an involuntary voiding attempt, the one or more therapy parameters may be adjusted accordingly to better control the patient's urinary or fecal incontinence.

The input mechanism that generates the electrical signal based on the patient defined action may be, for example, a multiple or single axis accelerometer or a strain gauge that produces a detectable change in electrical resistance based on the extent of deformation of the strain gauge, although other input mechanisms may be possible. For example, in some embodiments, a microphone may be used to detect the patient defined action, such as the tapping. The microphone may be similar to the microphone described above with respect to FIG. 2. The tapping of finger 202 on skin 218 refers to the motion of patient 10 pressing finger 202 downward into skin 218 located above or superior to device 212 and subsequently releasing finger 202 from skin 218, as indicated by the arrows in FIG. 12. Tapping skin 218 in this manner causes epidermis 206 and subcutaneous tissue 208 to compress and/or deflect in the direction of motion. This causes device 212 to be displaced from original location 204A to temporary location 204B for a period of time before returning to original location 204A. Original location 204A is indicated in FIG. 12 by the solid outline of device 212 while the temporary location 204B is indicated in FIG. 12 by the dashed outline of device 212'. When finger 202 is released from skin 218, epidermis 206 and subcutaneous tissue 208 return to their normal state and device 212 returns to its original location 204A. The distance device 212 travels along the axis of motion is represented by distance 210 in FIG. 12. The distance of this motion is labeled 210 in FIG. 12. Distance 210 may be approximately 1 millimeter (mm) to approximately 20 mm or on the order of approximately 1 mm. Accordingly, the accelerometer may be positioned on or within the housing of device 212 and may be capable of detecting movement of the device on the order of approximately 1 mm to approximately 20 mm.

Using a single axis accelerometer as the input mechanism for device 212 may provide certain advantages. For example, since a single axis accelerometer translates motion along a single axis into an electrical signal, it may be less likely to misconstrue other motions as tapping. In other words, the single axis accelerometer generates an electrical signal based on motion along a single axis. Therefore, motion along any other axis is not translated into an electrical signal. As a result, it is less likely that other patient motions that result in motion of device 212, such as jumping, sitting, standing, and the like, will be misinterpreted as input, i.e., tapping or other motions for identifying a voiding event as a controlled or involuntary event. Further, a single axis accelerometer may provide a less complex and more power efficient implementation than would otherwise be possible with a multiple axis accelerometer.

In operation, one or more taps may be used to identify a voiding event as a controlled or involuntary event. Each tap may also be referred to as an input event in this disclosure. In one example embodiment, a single tap may indicate that a voiding event was a involuntary event and two or more taps may indicate that a voiding event was an involuntary or incontinence event. In other embodiments, any two tapping patterns could be used to identify an involuntary voiding event from a voluntary event.

In other example embodiments, other characteristics of one or more input events may be used to identify a voiding event as a controlled or involuntary event. Other example characteristics include the duration of an input event, frequency of input events, pattern of input events, and the like. The duration of an input event is defined in this disclosure as the duration of time for which device 212 is displaced to temporary position 204B (indicated as device 212' in FIG. 12). In other words, the duration of the input event may be viewed as the period of time that the patient presses finger 202 into skin 218. For example, when device 212 detects that it was displaced to temporary position 204B for a threshold amount of time or greater, device 212 may record voiding information that indicates a voiding event was involuntary. On the other hand, when device 212 detects that it was displaced to temporary position 204B, but for less than a threshold amount of time, device 212 may record voiding information that indicates a voiding event was voluntary. In this way, an input event with a first predefined duration may be used to identify a controlled voiding event and an input event with a second predefined duration longer than the first predefined duration may be used to identify an involuntary voiding event. As an example, the first predefined duration may be within a range of approximately 1 second or less and the second predefined duration may be within a range of approximately greater than approximately 1 second and less than approximately 3 seconds. Other time durations may be used. In this way, a single input event can be used to identify a voiding event as a controlled or involuntary event.

Alternatively, instead of using the duration of an input event to identify the nature of a voiding event, the duration of an input event may be used to increase the reliability of detecting input events. In such cases the duration of an input event may be used to distinguish an input event from other motions that may be misconstrued as a characteristic input provided by the patient. In other words, since other motions of the patient, such as scratching, fastening a seat belt, and the like, may mimic the tapping input with respect to pressing skin 218 for a period of time, requiring an input event to have a defined duration may limit false positives.

In order to distinguish a characteristic "tap" from other movements that may be misconstrued as a characteristic input, the "tap" may involve pressing at location 212 for a period of time. By pressing for a characteristic period of time, this input may be distinguished from other actions that may be misconstrued as characteristic input. This may, for example, be useful for distinguishing displacement caused by sitting and standing. Sitting and standing may displace device 212 in the same way a characteristic patient input, but displaces device 212 for an extended period of time. In other words, a characteristic input displaces device 212 from its current position to a temporary position for a relatively short period of time, followed by returning to the original position. In contrast, sitting down may displace device 212 from its original position to a second position. Device 212 may, however, remain in this second position for a relatively extended period of time in comparison to the characteristic input. Again, the duration device 212 remains in the temporary position 204B may be compared to a threshold time period stored within a memory of device 212 in order to determine whether an input was intended to be an input.

The frequency of input events may be used to identify the nature of a voiding event by using different frequencies to distinguish between a controlled and an involuntary event. The frequency is defined as the time between two or more successive taps or input events. Therefore, a involuntary event may be identified by two or more taps characterized by a first frequency and an involuntary event may be identified by two or more taps characterized by a second frequency greater than the first frequency. For example, a involuntary event may be identified by two taps separated by a period of time of approximately half a second or less. In contrast, an involuntary event may be identified by two taps separated by a period of time of approximately a second or more. In this case, the involuntary event may be viewed as being similar to a "double click" of a mouse. In this way, multiple taps are required to provide input. Using multiple taps to identify the nature of a voiding event may be beneficial because it may prevent device 212 from misconstruing other motions as characteristic input provided by the patient.

In other example embodiments, a pattern of input events may be used to identify a voiding event as a controlled or involuntary event. In such embodiments, a pattern of input events may be defined as the temporal relationship between more than two input events. For example, a pattern may include three input events. In this case, one example pattern may be characterized by a short time period between the first and second input events and a longer time period between the second and third input events. Another example pattern may be characterized by a long time period between the first and second input events and a shorter time period between the second and third input events. A patterned input event may also be utilized to differentiate between intentional data entry, i.e., a patient defined action, and device movement resulting from normal patient actions, such as sitting and other patient actions that may otherwise be misconstrued as intentional data entry.

Device 212 may operate in an initial learning or calibration mode that trains patient 10 to enter the patient defined actions. For example, in a clinical setting device 212 may be programmed to enter the learning mode. In the learning mode, device 212 may expect certain patient defined actions and provide an indication if the patient defined actions were correctly detected. As an example, patient 10 may enter a specified patient defined action, such as a patterned input event that corresponds to identifying a voiding event as a voluntary event. Upon receiving the input event, device 212 may provide an audible alert or transmit data to an external monitoring device, such as a patient or clinician programmer, that prompts patient 10 whether the input was received correctly or incorrectly. Patient 10 may enter the input event several times in order to learn or become accustomed to the temporal and pressure characteristics of the input event that are required for proper detection by device 212. In other words, patient 10 can repeatedly enter an input event until the patient has learned to enter the input event correctly. This training mode may be important for patient 10 to easily and reliably provide input to identify the nature of voiding events.

In addition, the lack of input may be used to identify the nature of an event in some example embodiments. For example, a single tap may indicate that a voiding event was controlled and lack of an input may indicate the event was involuntary. In other examples, lack of input may be used to reduce the number of false positives. A false positive occurs when device 212 falsely detects that a voiding event occurred. In the event that a voiding event is detected, device 212 may be configured to expect an input from the patient. The input may be entered within a time frame following the detection of an event. This time frame may allow sufficient time for the patient to get to a restroom following an involuntary event so that the patient may deal with the involuntary event and enter input in privacy. However, if the patient does not provide input within the time frame, then the event is identified as a false positive.

This may be advantageous because it limits the motions that may be misconstrued by device 212 as characteristic input. That is, since device 212 expects input a short time period after detecting a voiding event, other motions that may normally be indistinguishable from characteristic input are not registered because they do not occur during the time window of interest. For example, following a detected voiding event, device 212 may examine the signal generated by the accelerometer over a window of time. This window may be less than approximately five seconds, less than approximately 10 seconds, or less than approximately a minute. In any case, it is unlikely that other motions that could be misconstrued as a patient input will occur during this time window thereby further increasing the confidence in the signal generated by the accelerometer within device 212. In the case that patient 10 is aware of a an involuntary voiding event, the lack of input may be used to identify the event as an involuntary event. Alternatively, the event may simply not be identified as a controlled or involuntary event to avoid confusion with the case that patient 10 forgot to enter input.

In some embodiments, device 212 may also provide an audible or other patient detectable alert as a reminder to the patient to enter input. As one example, device 212 may provide a beep or other sound that can be heard by patient 10 after a voiding event is detected. This beep may serve as a reminder to patient 10 to provide input to identify the voiding event. Alternatively, or in addition to beeping, device 212 may vibrate in a way that can be detected by the patient. In this manner, device 212 may reduce the likelihood that patient 10 forgets to provide input to identify the nature of a voiding event and, therefore, may reduce false positives.

It is recognized that the location at which device 212 is implanted may have a significant impact on performance of the device. For example, the performance of device 212 with respect to detecting a voiding event may be dependent on the proximity of the implant site to the source of the sound that is used to detect a voiding event. At the same time, the performance of device 212 with respect to identifying a voiding event as a controlled or involuntary event may be dependent on the on the depth at which device 212 is implanted within subcutaneous tissue 208. In other words, implanting device 212 in close proximity to the bladder or urinary tract of the patient and shallow in subcutaneous tissue 208, i.e., just under epidermis 206, may increase the accuracy and reliability of device 212 of detecting voiding events and identifying voiding events based on input received from the patient.

It should be understood that the embodiment described with respect to FIG. 12 is one of various example embodiments that may be used to identify the nature of a voiding event based on a patient defined action. In other example embodiments, the microphone may be used to detect a voiding event and receive input from the patient to identify the nature of the voiding event. In such an example, tapping skin 212 may produce a noise that is detected by the microphone. The sound produced by the tapping is translated into data by the microphone. Accordingly, a device in accordance with this embodiment may utilize two different signal processing techniques. A first technique may be used to detect a voiding event. This technique may be employed substantially continuously. Upon detecting a voiding event however, a second processing technique may be used. This second processing technique may be configured to detect the sound produced by tapping skin 212.

Identifying a voiding event as a controlled or involuntary event based on input received from the patient as described in this disclosure may provide certain advantages. One advantage is that the automatic voiding diary may be more accurate than a written or electronic voiding diary in which the patient manually enters data. In particular, device 212 may include features, e.g., alert features, which remind the patient to enter data in response to detecting a voiding event. This may reduce the likelihood that the patient forgets to enter input and, thus, result in a more complete voiding diary.

In some embodiments, voiding information generated by device 212 may be used to automatically adjust therapy parameters based on the input received from the patient, and in particular, upon detecting an involuntary voiding event by associating a voiding event with patient input indicating the event was involuntary. Device 212 may include a therapy module or may be coupled (wirelessly or via conductors) to a therapy delivery device. In embodiments in which device 212 is coupled to a therapy delivery device, a processor within device 212 may transmit a signal to the therapy delivery device indicating a request for a therapy parameter adjustment. Alternatively, the processor within device 212 may merely transmit the therapy information to the therapy delivery device, which may then process the information to determine whether to adjust therapy and if so, the adjustments to the therapy parameters. Therapy parameters may be adjusted to increase the intensity of therapy in response to detecting an involuntary voiding event. In this way, the therapy may be increased, for example by increasing stimulation current amplitude or stimulation voltage amplitude, until the patient no longer experiences involuntary voiding events or manually adjusts the parameters because the therapy is uncomfortable.

Figure 13:
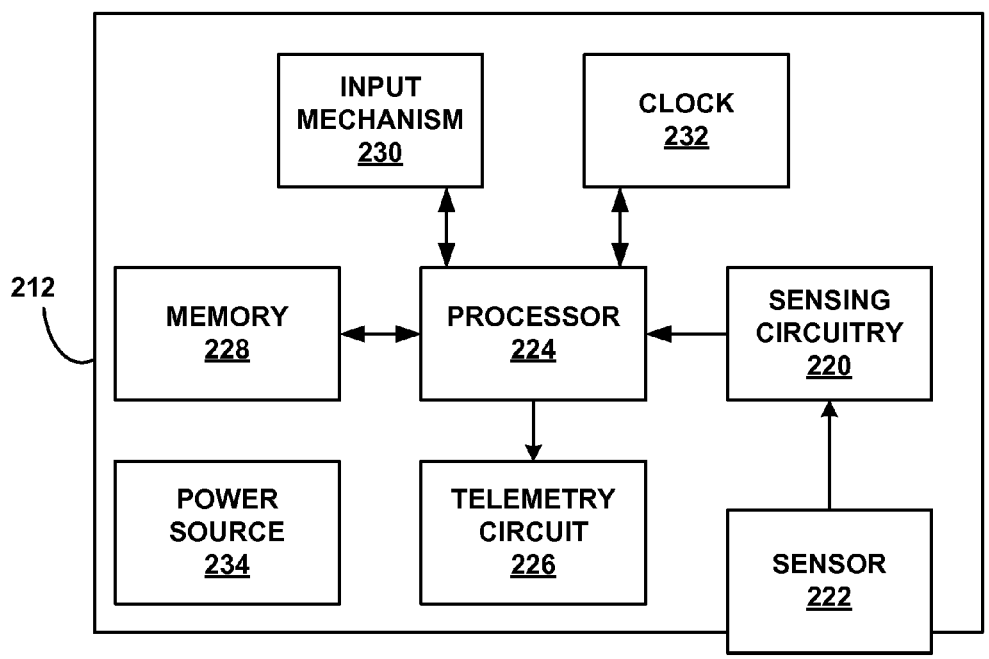
FIG. 13 is a schematic diagram illustrating various components of the example IMD in FIG. 12.

FIG. 13 is a block diagram illustrating various components of device 212. In the illustrated example of FIG. 13 device 212 includes sensing circuitry 220, sensor 222, processor 224, telemetry module 26, memory 228, input mechanism 230, clock 232, and power source 234, which are substantially similar to sensing circuitry 90, sensor 92, processor 90, telemetry module 96, memory 98, clock 112, and power source 114, respectively, of device 84 of FIG. 5. Thus, device 212 operates in a similar fashion as automatic voiding diary 84, but includes the additional features described in FIG. 12.

In general, input mechanism 230 generates an electrical signal in response to patient defined input, such as tapping as described in FIG. 12. As previously described, input mechanism 230 may be a single or multiple axis accelerometer located on or within the housing of device 212. Processor 224 processes the output of input mechanism 230 to generate identification information and stores the identification information in memory 228. Processor 224 may also control telemetry circuitry 226 to wirelessly transmit the identification information, as well as other voiding information, to an external device, such as patient and clinician programmer 16 and 18, respectively.

Figure 14:
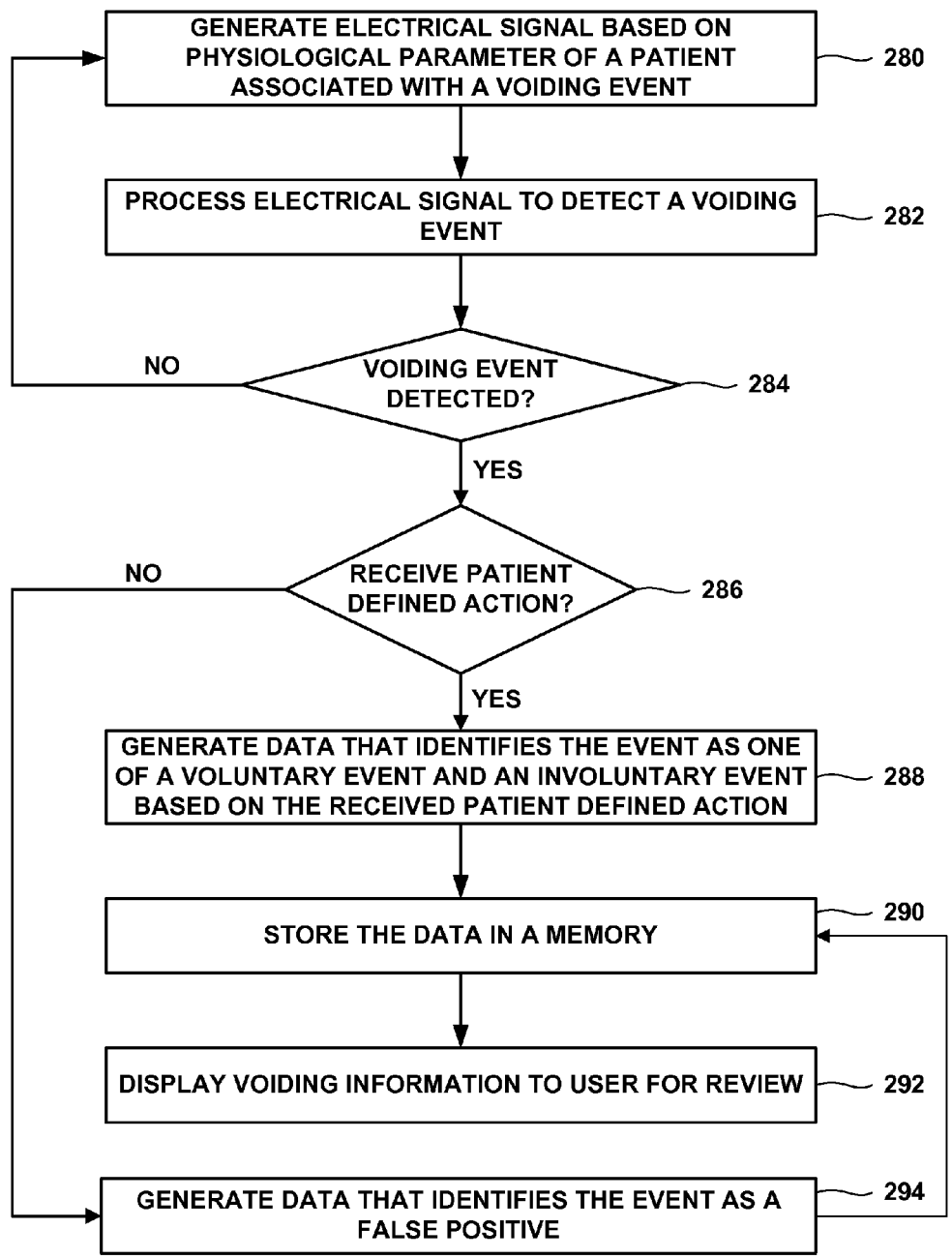
FIG. 14 is a flow diagram an example technique for recording voiding information based on a patient defined action.

FIG. 14 is a flow diagram illustrating an example technique utilized by device 212 for identifying a voiding event as a voluntary or involuntary event based on a patient defined action. The flow diagram begins with device 212 generating an electrical signal based on a parameter associated with a voiding event (280). For example, the parameter may be a sound that is associated with voiding events or a physiological parameter associated with voiding, such as bladder pressure. In this case, device 212 includes a microphone as previously described in this disclosure. However, other parameters may also be used to detect voiding events. As an example, device 212 may include pressure sensors, flow sensors, strain gauges, wetness sensors, or other sensors that generate electrical signals that can be used to detect voiding events.

In any case, device 212 processes the electrical signal to detect a voiding event (282). Processing the electrical signal may, for example, involve comparing the electrical signal to a signal template stored in memory as previously described in this disclosure or comparing an amplitude of the electrical signal to a threshold value. Device 212 continues to monitor the electrical signal generated by the microphone or other sensor when a voiding event is not detected ("NO" branch of decision block 284). However, upon detecting a voiding event ("YES" branch of decision block 284), device 212 monitors the output of the accelerometer to receive a patient defined action (286).

As previously described, device 212 may monitor the output of the accelerometer for a pre-determined window of time following the detection of a voiding event. If device 212 has not received a patient defined action within the window of time ("NO" branch of decision block 286), device 212 generates data that identifies the detected voiding event as a false positive (294). The false positive data may be stored within memory (290). In other embodiments, device 212 may generate data that simply indicates that the patient did not enter input. In any case, the identification data (or "identification information") is stored in memory (290) and may be displayed to a user for review (292).

When device 212 receives a patient defined action within the time window ("YES" branch of decision block 286), a processor within device 212 may associate the input from the patient via the patient defined action with a voiding event, and generate data that identifies the event as one of a voluntary and an involuntary event based on the received patient defined action (288). Device 212 may then store the identification data (or "identification information") in memory (290). The identification data may be a value, flag, or signal that is stored or transmitted to whether a detected voiding event was controlled (i.e., voluntary) or involuntary. In some embodiments, voiding information, including the identification information or data, is displayed to a user for review (292). In order to display the voiding information to a user, such as a patient or clinician, device 212 may wirelessly transmit the voiding information to an external device, such as a patient or clinician programmer, or another computing device. In other embodiments, device 212 may merely associate the receipt of the patient input via the patient-defined action with a voiding event, and the information may be transmitted to another computing device to determine whether the input indicates the voiding event was voluntary or involuntary.

As previously described, in other embodiments, a patient defined action confirming that a detected voiding event was in fact a voiding event may be obtained through techniques other than device 212. For example, the patient may provide feedback via a patient programmer or another external computing device, such as by responding to a prompt from the patient programmer or depressing a button dedicated to such confirmation input.

Systems and methods that include a input mechanism that is configured to receive a patient defined action from a patient in order to determine whether a voiding event was voluntary or involuntary is described in commonly-assigned U.S. patent application Ser. No. 11/755,587 by Martin T. Gerber et al., entitled, "VOIDING EVENT IDENTIFICATION BASED ON PATIENT INPUT," and filed on the same date as the present disclosure, the entire content of which is incorporated herein by reference.

Figure 15A:
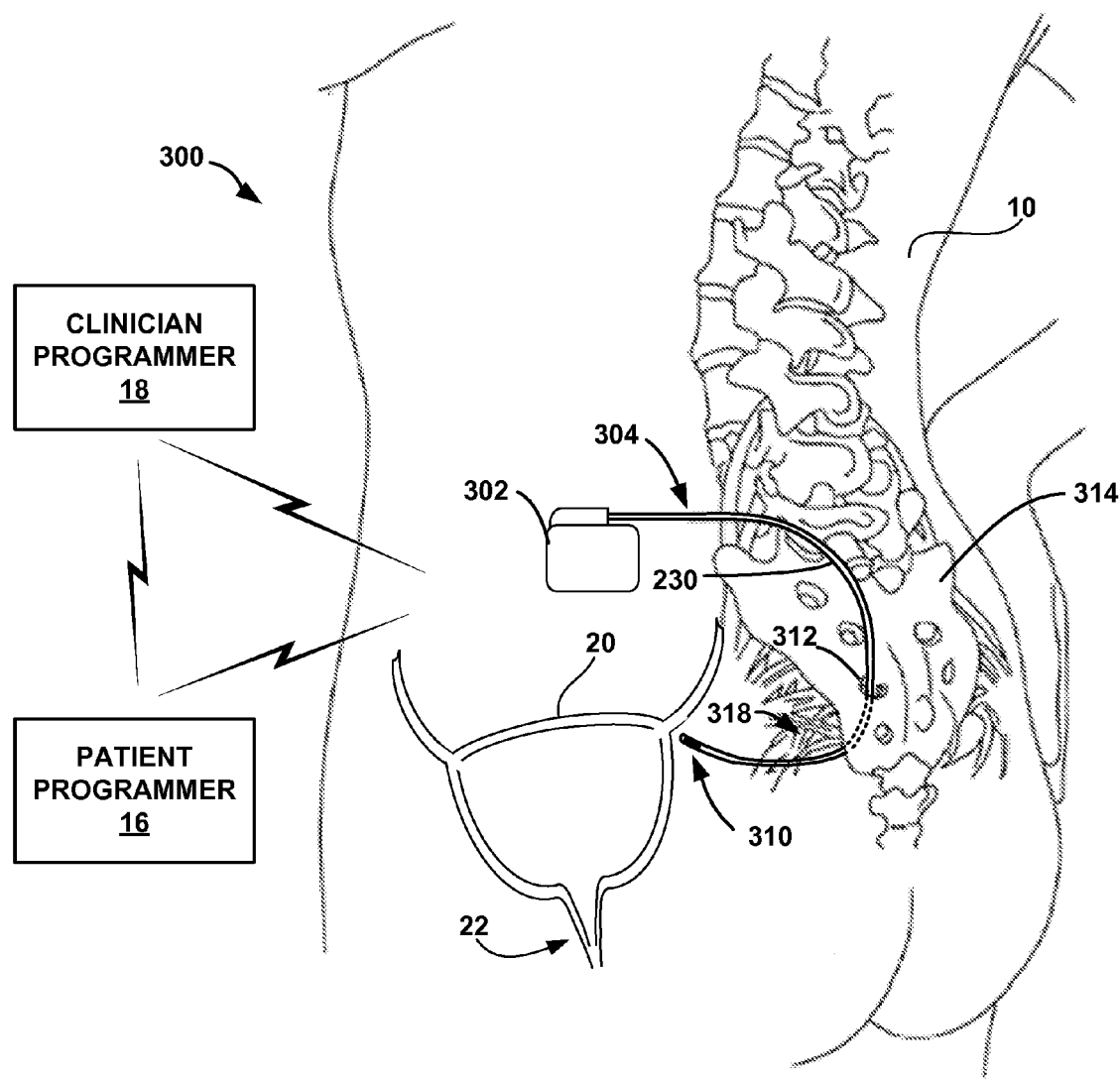
FIGS. 15A and 15B are schematic diagrams illustrating a system including an IMD configured to operate as an automatic voiding diary and coupled to an implantable medical lead that carries one or more sensors for detecting urinary and fecal voiding events, respectively.

FIG. 15A is a schematic diagram illustrating an automatic urinary voiding diary system 300. System 300 includes IMD 302 coupled to implantable medical lead 304. Lead 304 has an elongated body that extends between a distal end carrying sensor 310 and a proximal end coupled to IMD 302. In general, IMD 302 is configured to operate as an automatic voiding diary that detects urinary voiding events based on a sensor signal received via lead 304 and records voiding information for detected urinary voiding events. In some embodiments, IMD 302 may also be configured to operate as therapy delivery device, such as an electrical stimulator, drug pump, or both. In embodiments in which IMD 302 delivers therapy to the patient, lead 304 may be configured as a combination lead, i.e., a lead that includes sensor 310 and therapy element. For example, lead 304 may include both sensor 310 and electrical stimulation electrodes, or one or more additional leads may be coupled to IMD 302, e.g., to deliver electrical stimulation, drug therapy, or both.

Although lead 304 is illustrated in FIG. 15A as carrying a single sensor, i.e., sensor 310, in other embodiments, lead 304 may carry multiple sensors. The sensors may include one or more microphones, pressure sensors, flow sensors, strain gauges, sensing electrodes, temperature sensors, any other type of sensor used for generating a signal indicative of a parameter associated with voiding events, or any combination thereof. Lead 304 may carry two or more different types of sensors. IMD 302 receives an electrical signal generated by sensor 310 (and any other sensors carried by lead 304) and processes the electrical signal to detect urinary voiding events, and records the voiding events in a voiding diary.

In the embodiment shown in FIG. 15A, lead 304 is positioned so that its distal end and, more particularly, sensor 310 is proximate to bladder 20. However, it should be understood that lead 304 may be implanted at other target sensing sites suitable for sensing parameters associated with urinary voiding events. Accordingly, the location of lead 304 within patient 10 may depend on the type of sensor 310.

IMD 302 processes the electrical signal generated by sensor 310 to detect voiding events. In particular, IMD 302 may operate as previously described in this disclosure. For example, sensor 310 may be viewed as the microphone that generates an electrical signal based on sounds associated with voiding events. Accordingly, IMD 302 may process the sensor signal to detect voiding events using the previously described signal processing techniques, such as filtering techniques for removing unwanted signal components, correlation or comparison techniques that utilize a signal template, and low power techniques that combine a sleep or low power state and one of the previously described techniques for detecting voiding events.

System 300 may be particularly advantageous in embodiments in which system 300 is configured to deliver therapy to patient 10 to treat urinary incontinence. Delivering electrical stimulation to the S3 sacral nerve may help treat urinary incontinence. In such embodiments, lead 304 may be configured to also deliver electrical stimulation, drug therapy, or both, at target stimulation site 318 proximate to the S3 sacral nerve. Lead 304 may include one or more stimulation electrodes (not shown) or have one or more openings (not shown) for delivering drug therapy. The stimulation electrodes and/or openings for delivering drug therapy may be located on lead 304 such that when 304 is fully implanted in patient 10 as shown in FIG. 15A, sensor 310 is positioned proximate to bladder 20 and the stimulation electrodes and/or openings are proximate to target stimulation site 318. In this case, the trauma experienced by the patient during implantation of system 300 is reduced because only a single lead is required to be implanted to achieve both sensing of voiding events and therapy delivery to treat incontinence.

In embodiments in which lead 304 only carries sensor 310 and a separate lead is used to deliver therapy, certain advantages may still be achieved. In particular, because lead 304 carries sensor 310 proximate to its distal end, lead 304 may be implanted without requiring an additional incision. For example, the lead or leads that deliver therapy may be implanted within patient 10 through an incision and positioned at a target stimulation site, such as target stimulation site 318 proximate to the S3 sacral nerve. When the therapy leads have been implanted, lead 304 may be implanted through the same incision and positioned at a different target site. That is, lead 304 is introduced into the S3 sacral foramen 312 of sacrum 314 in the same way that the therapy leads are introduced. However, lead 304 may be advanced towards bladder 20 and positioned so that sensor 310 is proximate to bladder 20 as shown in FIG. 15A. Thus, no additional incisions are required and the trauma experienced by patient 10 is reduced.

As shown in FIG. 15A, system 300 also may include a clinician programmer 18 and a patient programmer 16. Clinician and patient programmers 18 and 16 may be handheld computing devices that enable a clinician and patient 10, respectively, to view voiding information and control delivery of therapy. For example, using clinician programmer 18, the clinician may specify electrical stimulation or drug therapy parameters.

Clinician programmer 18 supports telemetry (e.g., radio frequency telemetry) with IMD 302 to upload electrical stimulation parameters and, optionally, download operational or physiological data stored by electrical stimulator 12. In this manner, the clinician may periodically interrogate IMD 302 to evaluate efficacy and, if necessary, modify the stimulation parameters. Patient 10 may use patient programmer 16 to start, stop or adjust therapy. In particular, patient programmer 16 may permit patient 10 to adjust stimulation parameters such as duration, amplitude, pulse width and pulse rate, within an adjustment range specified by the clinician via clinician programmer 18, or select from a library of stored stimulation therapy programs. Patient and clinician programmers 16 and 18 communicate via cables or a wireless communication, as shown in FIG. 15A. For example, clinician programmer 18 and patient programmer 16 may communicate with each other and IMD 302 using any of a variety of local wireless communication techniques, such as RF communication according to the 802.11 or Bluetooth specification sets, infrared communication, e.g., according to the IrDA standard, or other standard or proprietary telemetry protocols.

Figure 15B:
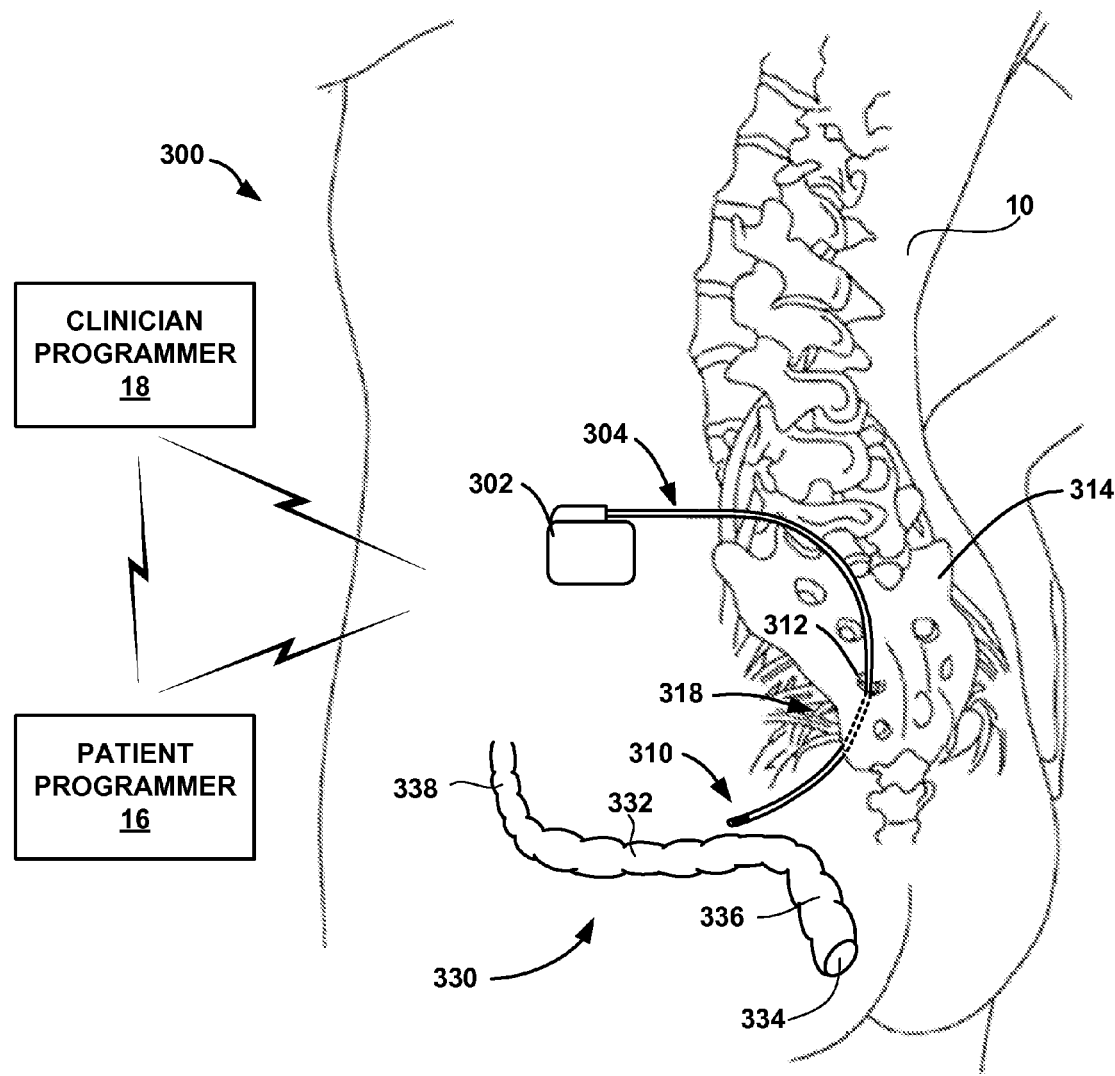

In FIG. 15B, system 300 is configured to operate as a fecal voiding diary system in which lead 304 is positioned to proximate to intestines 330. Positioning lead 304 and, more particularly, sensor 310 proximate to intestines 330 instead of bladder 20 enables lead 304 to be used for detecting fecal voiding events instead of urinary voiding events. Thus, system 300 in FIG. 15B operates as described with respect to FIG. 15A.

The purpose of FIG. 15B is to describe the unique features of detecting fecal voiding events. These unique features relate to the positioning of lead 304 and the type of sensor used for sensor 310. Sensor 310 may be a microphone, strain gauge, electromyography (EMG) sensor, accelerometer, piezoelectric sensor, or other sensor that generates an electrical signal based on a sound, pressure, motion, or turbulence caused by the movement of fecal matter in the intestines, rectum, or bowel during a voiding event. Lead 304 may be positioned, for example, such that sensor 310 is located proximate to a portion of the bowel, large intestines, proximate to the sacrum (e.g., below the sacrum), anus, rectum, descending colon, or sigmoid colon.

As an example, lead 304 may be implanted so that sensor 310 is implanted proximate to a portion of the sigmoid colon as shown in FIG. 15B. In FIG. 15B, rectum 336, sigmoid colon 332, and descending colon 338 are shown. Specifically, sigmoid colon 332 and rectum 336 are depicted such that their positions relative to one another form a "valve" or "fold" that prevents fecal matter from entering rectum 336. During a fecal voiding event, however, sigmoid colon 332 and rectum 336 may shift from the illustrated positions to positions that open the valve or fold thereby allowing fecal matter in sigmoid colon 332 to pass to rectum 336 and exit anus 334. In the illustrated example of FIG. 15B, sensor 310 generates an electrical signal based on the motion of sigmoid colon 332 and rectum 336 relative to the bulk of patient 10. In this case, sensor 310 may comprise one or more strain gauges or accelerometers disposed along a distal portion of lead 304.

It should be understood that although FIGS. 15A and 15B depict a single lead, more than one lead may be used to detect urinary and fecal voiding events, respectively. Rather, the purpose of FIGS. 15A and 15B are to illustrate one example embodiment of the invention and should not be considered limiting of the invention as broadly described in this disclosure.

Figure 16:
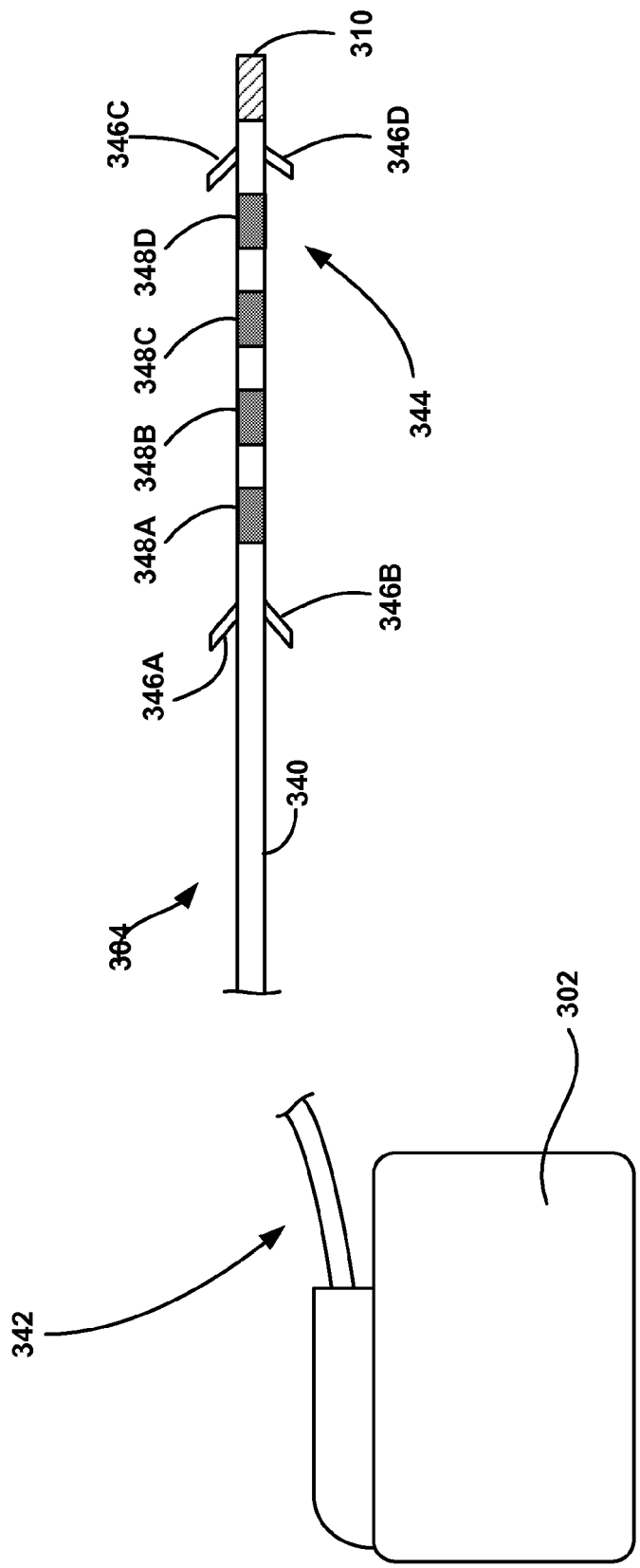
FIG. 16 is a perspective view of an example medical lead that may be used for detecting voiding events and deliver therapy to a patient for urinary or fecal incontinence.

FIG. 16 is a detailed perspective view illustrating an embodiment of lead 304, which includes lead body 340 extending between proximal end 342 and distal end 344, sensor 310 positioned proximate to distal end 344, fixation elements 346A-D (collectively referred to as "fixation elements 346"), and stimulation electrodes 348A-D (collectively referred to as "stimulation electrodes 348"). Stimulation electrodes 348 are electrically coupled to a therapy module within IMD 302 via conductors disposed within lead 304. In particular, lead 304 may include a set of proximal electrical contacts at proximal end 342 which couple to IMD 302 directly or indirectly via a lead extension. In some embodiments, electrodes 348 are coupled to separate conductors, which allows separate stimulation signals to be delivered to each electrode 348. In other embodiments, two or more electrodes 348 may be coupled to a common conductor.

Lead 304 is illustrated in FIG. 16 with a single sensor 310. However, in other embodiments, more than one sensor maybe located proximate to distal end 344 of lead 304. As previously described with respect to FIG. 15A, sensor 310 may be any sensor that generates an electrical signal based on a parameter associated with a voiding event, such as a microphone, a pressure sensor, a flow sensor, a strain gauge, and the like.

In FIG. 16, electrodes 348 are positioned adjacent to sensor 310 at distal end 344, but may generally be located anywhere along lead body 340. Positioning electrodes 348 proximate to sensor 310 may be advantageous when the target stimulation and sensing site are in close proximity to each other. In other embodiments in which target stimulation and sensing site are in close proximity to each other, sensor 310 may be located between one or more of electrodes 348. Alternatively, in embodiments that have multiple sensors located at distal end 344, electrodes 348 and the sensors may be interspersed with each. For example, electrodes 348 and the sensors may be arranged in an alternating fashion.

In other embodiments, electrodes 348 may be disposed on a medially located portion of lead body 340 between distal end 344 and proximal end 342, rather than proximate to distal end 344 of lead 304. This may be advantageous when lead 304 is implanted such that sensor 310 is located proximate to a target sensing site, such as the bladder or intestines of the patient, and electrodes are located proximate to a remotely located target stimulation site relative to the target sensing site, such as the S3 sacral nerve. In additional embodiments, electrodes 348 may be disposed proximate to proximal end 342 of lead body 340.

Fixation elements 346 may help fix lead 304 to surrounding tissue and minimize migration of sensor 310 and electrodes 348 from their respective target sensing and stimulation sites. Fixation elements 346 may be located adjacent to both sensor 310 and electrodes 348 or, alternatively, fixation elements 346 may only be located proximate to one of sensor 310 and electrodes 348. In embodiments in which sensor 310 is located at distal end 344 and electrodes 348 are located at a different position along lead body 340, fixation elements may preferably be located adjacent to both sensor 310 and electrodes 348. Moreover, it may be advantageous for fixation elements to be located both proximally and distally relative to sensor 310 and electrodes 348. In this manner, fixation elements 346 may prevent sensor 310 and electrodes from migrating and, therefore, prevent a degradation in the performance of lead 304.

Fixation elements 346 may be, for example, tines, barbs, hooks, and so forth. Alternatively, lead 304 may be sutured to surrounding tissue in order to secure the position of sensor 310 and electrodes 348. Suturing, however, is typically more invasive then fixation elements 346. In some cases, fixation elements 346 or suturing lead 304 to surrounding tissue may not be beneficial at all implantation sites. Therefore, it should be understood that fixation elements 346 depicted in FIG. 16 are merely exemplary and the number and location of fixation elements 346 may be changed based on the implant site of lead 304.

An example of a lead including a sensor configured to generate a signal that varies as a function of a parameter associated with a voiding event, and thus, may be used to determine whether a voiding event occurred, is described in commonly-assigned U.S. patent application Ser. No. 11/755,578 by Martin T. Gerber et al., entitled, "IMPLANTABLE MEDICAL LEAD INCLUDING VOIDING EVENT SENSOR," and filed on the same date as the present disclosure, the entire content of which is incorporated herein by reference.

Figure 17:
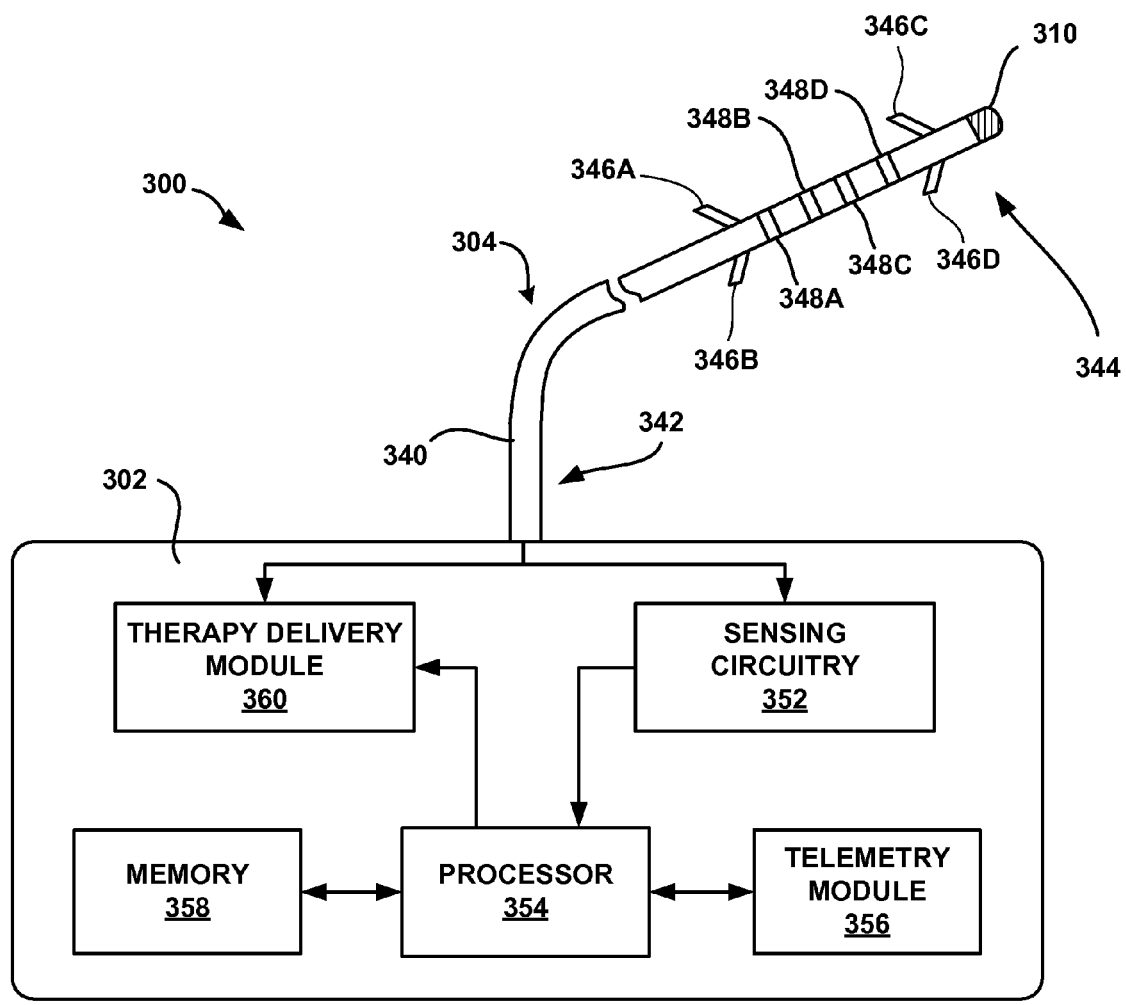
FIG. 17 is a block diagram illustrating various components of an IMD and the implantable medical lead of FIG. 16.

FIG. 17 is a block diagram illustrating various components of IMD 302 and lead 304 of system 300. IMD 302 is an implantable automatic voiding diary that includes lead 304 with a sensor 310 disposed at distal end 344. As shown in FIG. 17, IMD 302 includes sensing circuitry 352, processor 354, telemetry module 356, memory 358, and therapy delivery module 360. IMD 302 is substantially similar to IMD 12, which is shown and described with respect to FIG. 2. Thus, the description of sensor 42, sensing circuitry 40, telemetry module 46, and therapy delivery module 32 are substantially applicable to a description of sensor 310, sensing circuitry 352, telemetry module 356, and therapy delivery module 360, respectively. Similarly, processor 354 and memory 358 of IMD 302 are substantially similar to processor 44 and memory 46, respectively, of IMD 12.

Figure 18:
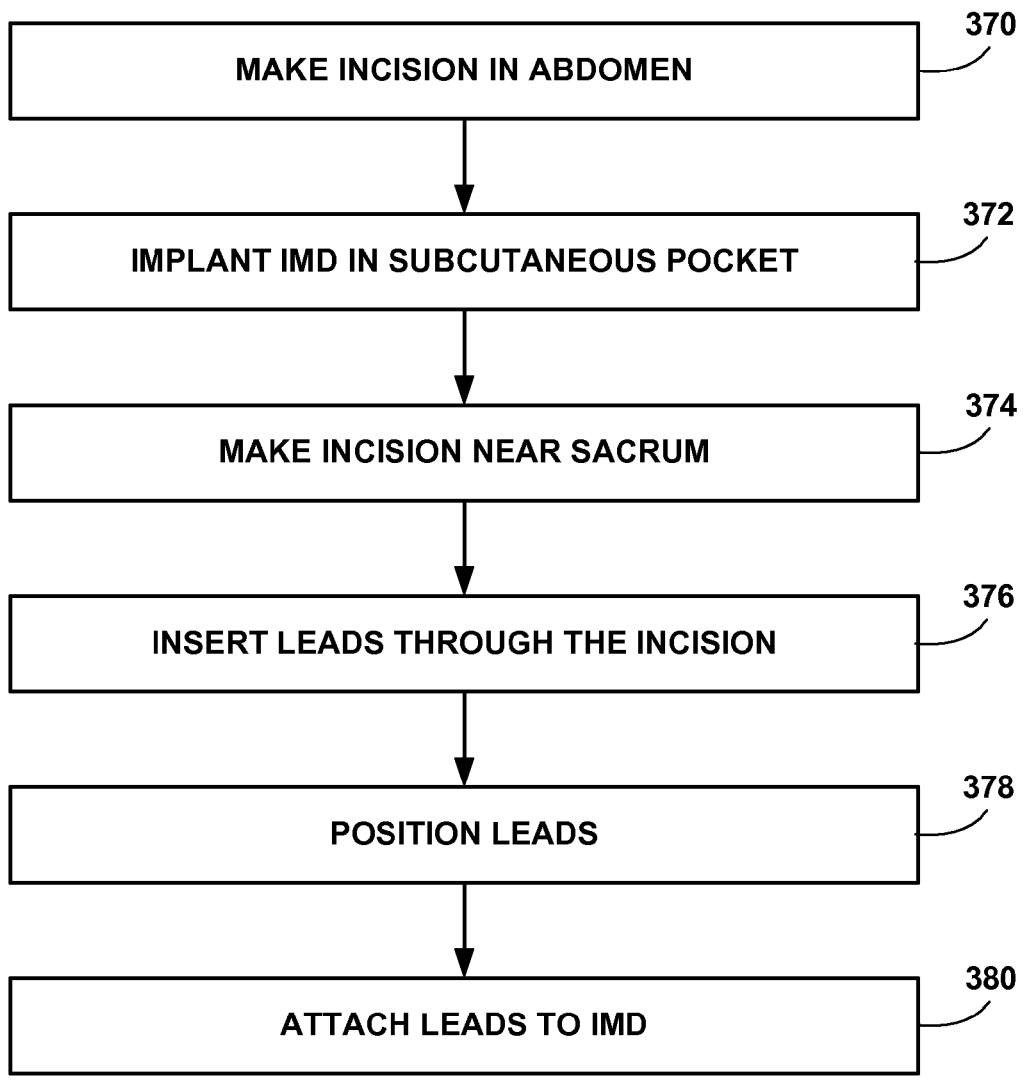
FIG. 18 is a flow diagram illustrating an example technique for implanting an implantable medical lead for detecting voiding events and delivering therapy to a patient for urinary or fecal incontinence.

FIG. 18 is a flow diagram illustrating an embodiment of a technique for implanting IMD 302 and lead 304 including a distal sensor 310 and stimulation electrodes 348 in the body of patient 10. In particular, the technique may be used to implant lead 304 by introducing lead 304 through a foramen of the sacrum. A clinician may make an incision in the abdomen (370) or other suitable area of the patient, such as the lower back or buttocks, where the incision is sized to receive IMD 302. Next, the clinician implants IMD 302 in a subcutaneous pocket (372) through the incision. The clinician may form the subcutaneous pocket in any region of patient 10, such as the abdomen. The location of the incision (370) may depend upon the desired implant site for IMD 302. Accordingly, in other embodiments, the incision and subcutaneous pocket may be made in other regions, such as the lower back of patient 10.

Upon implanting IMD 302, the clinician makes another incision near the sacrum (374) and inserts lead 304, as well as any additional leads, through this incision (376). Next, the clinician positions the leads (378), i.e., lead 304 and any additional leads, by introducing the leads through a foramen of the sacrum and guiding lead 304 to target stimulation site 318 (FIGS. 15A-B). As an example, the clinician may position lead 304 through sacral foramen 312 in sacrum 314 in order to reach target stimulation site 318 and the target sensing site, as shown in FIGS. 15A and 15B. The clinician may fine-tune the position of lead 304, such that sensor 310 is proximate to a portion of bladder 20 for sensing urinary voiding events or a portion of the intestines 330 for sensing fecal voiding events. In embodiments in which lead 304 also carries stimulation electrodes, the stimulation electrodes may be positioned proximate to target stimulation site 318, e.g., the S3 sacral nerve. In embodiments in which the clinician implants multiple leads within patient 10, the clinician may insert and position each of the leads separately. In some embodiments, the multiple leads may be inserted through a single incision thereby minimizing the trauma experienced by the patient.

After properly positioning lead 304 or multiple leads within patient 10 (378), the clinician may tunnel a proximal end 342 of lead 304 to IMD 302, and couple the proximal end 342 to IMD 302 (380). The clinician may then activate IMD 302 and proceed to monitor the condition of the patient via an external programmer and begin delivering or testing therapy as needed.

Various embodiments of the invention have been described. These and other embodiments are within the scope of the following claims.

The invention claimed is:

1. A system comprising:
    a microphone that generates an electrical signal based on a sound associated with a voiding event of a patient; and
    a processor that determines whether the voiding event occurred based on the electrical signal, wherein the processor generates voiding information upon detecting an occurrence of the voiding event;
    further comprising an implantable medical lead electrically coupled to the processor, wherein the implantable medical lead includes the microphone;
    wherein the implantable medical lead further comprises a stimulation electrode, and the system further comprising a therapy delivery module configured to deliver therapy to the patient via the stimulation electrode of the implantable medical lead to control at least one of urinary or fecal incontinence.

2. The system of claim 1, further comprising a memory that stores the voiding information generated by the processor.

3. The system of claim 2, further comprising an external computing device, wherein the external computing device comprises the memory.

4. The system of claim 3, wherein the external computing device receives the voiding information from the processor via wireless communication and presents the voiding information to a user via a display.

5. The system of claim 3, wherein the processor comprises a first processor and the external computing device comprises a second processor configured to receive an indication of whether the voiding event was a controlled event or an involuntary event, and associate the indication with the voiding event within the memory.

6. The system of claim 2, wherein the processor determines whether the voiding event occurred based on the electrical signal by at least one of comparing a characteristic of the electrical signal to a threshold value stored in the memory or comparing a sample of the electrical signal to a signal template stored in the memory.

7. The system of claim 6, wherein the characteristic of the electrical signal comprises a first power of one or more frequency components of the electrical signal, a second power associated with a portion of the electrical signal or an amplitude of the electrical signal.

8. The system of claim 1, further comprising a telemetry module configured to wirelessly transmit the voiding information to at least one of an external programmer or a therapy delivery device that delivers therapy to the patient to control at least one of urinary or fecal incontinence.

9. The system of claim 1, wherein the sound comprises an internal sound generated within the patient.

10. The system of claim 9, wherein the internal sound includes one or more of a first sound produced by a bladder of the patient, a second sound produced by a urinary tract of the patient, a third sound produced by a rectum of the patient, a fourth sound produced by intestines of the patient, a fifth sound produced by one or more organs of the patient or a sixth sound produced by tissue of the patient.

11. The system of claim 1, wherein the sound comprises an external sound generated external to the patient.

12. The system of claim 11, wherein the external sound includes one or more of a first sound produced by fluid being voided into a toilet, a second sound produced by the toilet flushing or a third sound produced by fluid being voided into an undergarment.

13. The system of claim 1, wherein the voiding information includes at least one of a portion of the electrical signal that includes a voiding signature, an indication of the occurrence of the voiding event or a time at which the voiding event was detected.

14. A method of creating a voiding diary for a patient, the method comprising:
    receiving an electrical signal from a microphone, wherein the microphone generates the electrical signal based on a sound associated with a voiding event;
    determining whether the voiding event occurred based on the electrical signal; and
    generating voiding information upon detecting the occurrence of the voiding event;
    wherein determining whether the voiding event occurred comprises:
    processing the electrical signal according to a first technique; and
    processing the electrical signal according to a second technique if the processing according to the first technique suggests the voiding event occurred.

15. The method of claim 14, further comprising storing the voiding information in a memory.

16. The method of claim 14, wherein the microphone is implanted within the patient.

17. The method of claim 14, further comprising delivering therapy to the patient to control at least one of urinary or fecal incontinence based on the voiding information.

18. The method of claim 14, further comprising adjusting one or more therapy parameters of a therapy delivered to the patient to control at least one of urinary or fecal incontinence based on the voiding information.

19. The method of claim 14, further comprising wirelessly transmitting the voiding information to a therapy delivery device or an external programmer.

20. The method of claim 14, wherein the sound includes an internal sound generated within the patient or an external sound generated external to the patient.

21. The method of claim 14, further comprising:
generating an example electrical signal in response to an actual voiding event; and
storing the example electrical signal as a signal template in a memory, wherein determining whether the voiding event occurred comprises comparing the electrical signal to the signal template.

22. The method of claim 14, wherein processing the electrical signal according to the first technique comprises comparing a characteristic of the electrical signal to a threshold value stored in the memory, and wherein processing the electrical signal according to the second technique comprises comparing a sample of the electrical signal to the signal template.

23. The method of claim 22, wherein the characteristic of the electrical signal comprises a first power of one or more frequency components of the electrical signal, a second power associated with a portion of the electrical signal or an amplitude of the electrical signal.

\* \* \* \* \*